(12) United States Patent
Kozel et al.

(10) Patent No.: US 8,192,720 B2
(45) Date of Patent: Jun. 5, 2012

(54) COMPOSITIONS AND METHODS FOR DETECTION, PREVENTION, AND TREATMENT OF ANTHRAX AND OTHER INFECTIOUS DISEASES

(75) Inventors: Thomas Kozel, Reno, NV (US); William Murphy, Reno, NV (US); Suzanne Brandt, Boise, ID (US); Bruce R. Blazar, Golden Valley, MN (US); Julie A. Lovchik, Albuquerque, NM (US); Peter Thorkildson, Reno, NV (US); Ann Percival, Reno, NV (US); C. Richard Lyons, Ft. Collins, CO (US)

(73) Assignee: Board of Regents of the Nevada System of Higher Education, on behalf of the University of Nevada, Reno, Reno, NV (US)

( * ) Notice: Subject to any disclaimer, the term of this patent is extended or adjusted under 35 U.S.C. 154(b) by 0 days.

(21) Appl. No.: 12/701,149

(22) Filed: Feb. 5, 2010

(65) Prior Publication Data
US 2010/0291092 A1 Nov. 18, 2010

Related U.S. Application Data

(62) Division of application No. 10/809,831, filed on Mar. 26, 2004, now Pat. No. 7,682,796.

(60) Provisional application No. 60/502,533, filed on Sep. 12, 2003, provisional application No. 60/529,625, filed on Dec. 16, 2003.

(51) Int. Cl.
*A61K 49/00* (2006.01)
*A61K 39/07* (2006.01)
*A61K 39/02* (2006.01)

(52) U.S. Cl. .... 424/9.2; 424/9.1; 424/130.1; 424/141.1; 424/150.1; 424/164.1; 424/184.1; 424/234.1; 424/246.1; 435/4; 435/7.1; 435/7.2; 436/501

(58) Field of Classification Search .................. 424/9.1, 424/9.2, 130.1, 141.1, 150.1, 164.1, 184.1, 424/234.1, 246.1; 435/4, 7.1, 7.2; 436/501
See application file for complete search history.

*Primary Examiner* — Rodney P. Swartz
(74) *Attorney, Agent, or Firm* — Ryan A. Heck; UNR-DRI Technology Transfer Office

(57) ABSTRACT

Compositions and methods for the detection, prevention, or treatment of anthrax or other infectious diseases. In one aspect, the present invention provides methods for immunizing humans or animals against *Bacillus anthracis* or other capsulated pathogens. The methods include administering a capsular polypeptide of a pathogen of interest and a CD40 agonist to a human or animal. The capsular polypeptide or the CD40 agonist is administered in such an amount or frequency that an immunoprotective response can be elicited in the human or animal against the pathogen of interest. In another aspect, the present invention provides methods of using passive immunization with anti-capsular polypeptide antibodies to prevent or treat infections caused by *Bacillus anthracis* or other pathogens. In yet another aspect, the present invention provides methods useful for diagnosis of anthrax by detection of capsular polypeptide in serum or other biological samples.

**9 Claims, 13 Drawing Sheets

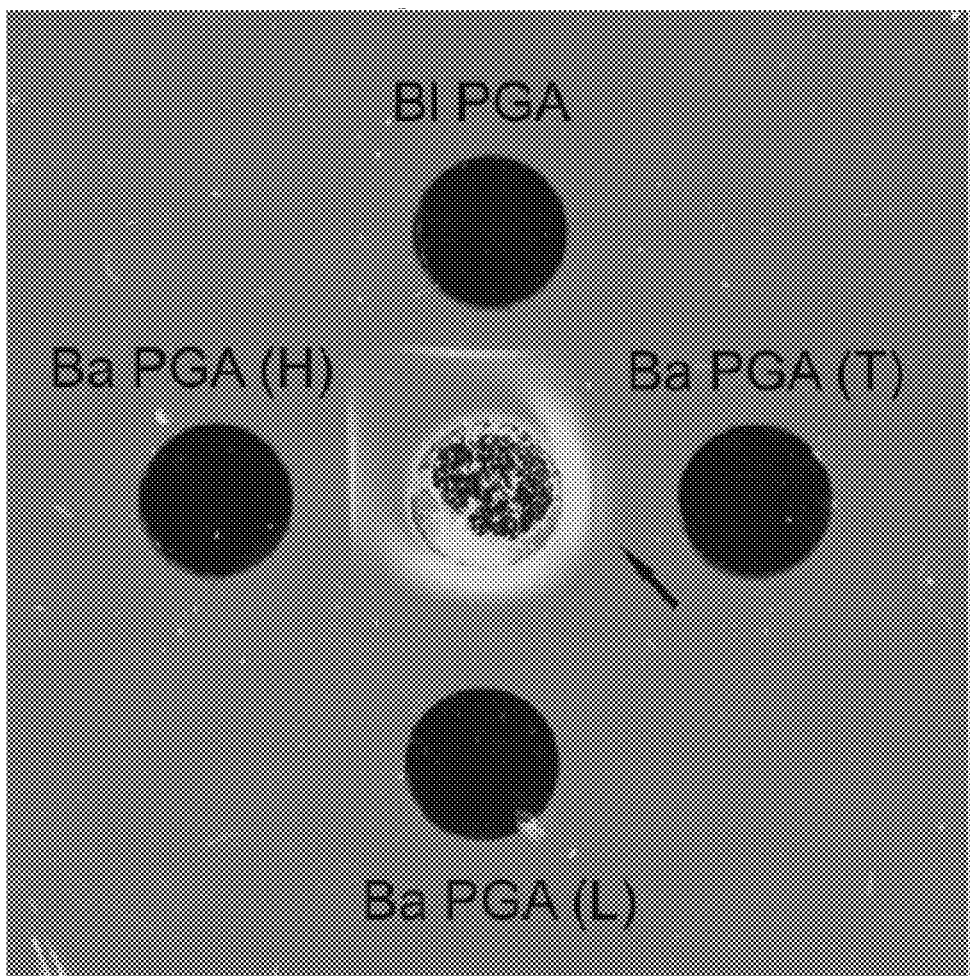
Figure 5A
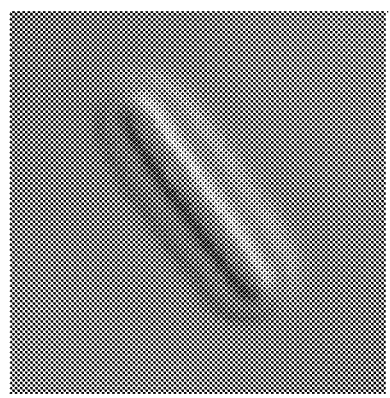 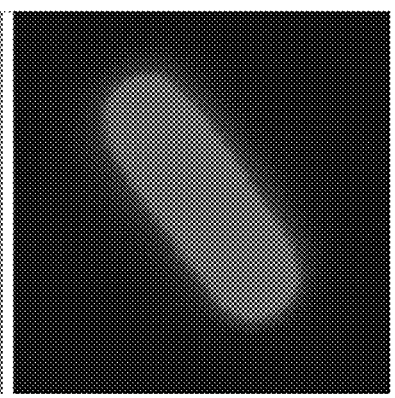
Figure 5B  Figure 5C

COMPOSITIONS AND METHODS FOR DETECTION, PREVENTION, AND TREATMENT OF ANTHRAX AND OTHER INFECTIOUS DISEASES

CROSS REFERENCE TO RELATED APPLICATIONS

This application is a divisional application of, and incorporates by reference, U.S. patent application Ser. No. 10/809,831, filed Mar. 26, 2004, now U.S. Pat. No. 7,682,796, which in turn claims the benefit of U.S. Provisional Patent Application Nos. 60/502,533 filed Sep. 12, 2003, and 60/529,625, filed Dec. 16, 2003.

STATEMENT OF GOVERNMENT SUPPORT

This invention was made with Government support under a grant from the National Institutes of Health, Grant No. AI-014209, and a grant from the Defense Advanced Research Program Agency, Grant No. N00178-01-C-3069. The Government has certain rights in the invention.

REFERENCE TO RELATED APPLICATIONS

This application claims priority from U.S. Provisional Application entitled "Production of Monoclonal and Polyclonal Antibodies Reactive with the Capsular Polypeptide of *Bacillus anthracis* and Uses Thereof" (by Thomas R. Kozel, et al.) and U.S. Provisional Application filed Dec. 16, 2003 and entitled "Monoclonal Antibodies to *Bacillus anthracis* Capsular Antigen for Immunoprotection in Anthrax and Detection of Antigenemia" (by Thomas R. Kozel, et al.).

FIELD OF THE INVENTION

The present invention relates to vaccine compositions and immunization schemes for protecting humans or other vertebrates from anthrax or other infectious diseases. The present invention also relates to antibodies reactive with capsular polypeptides of *Bacillus anthracis* or other pathogens and methods of using these antibodies for the detection, prevention, or treatment of anthrax or other diseases.

BACKGROUND OF THE INVENTION

Anthrax is an acute infectious disease caused by the spore-forming bacterium *Bacillus anthracis*. Anthrax most commonly occurs in wild and domestic lower vertebrates (e.g., cattle, sheep, goats, camels, antelopes, or other herbivores), but it can also occur in humans when they are exposed to infected animals or tissues from infected animals. In addition, *Bacillus anthracis* is one of the most important pathogens on the list of bioterrorism threats. The human $LD_{50}$ for inhalational exposure is about 8,000 to 40,000 spores, or one deep breath at site of release.

Anthrax infection can occur in at least three forms—namely, inhalational, cutaneous, and gastrointestinal. Inhalation anthrax occurs in several discrete steps. Endospores of *Bacillus anthracis* are taken up by macrophages at the site of initial infection and can be transported to regional lymph nodes. The spores germinate inside the phagolysosome to become vegetative bacteria which can escape from the phagolysosome and replicate within the cytoplasm. Vegetative cells are released into the extracellular milieu and enter the circulation where the vegetative cells grow extracellularly to levels as high as $10^8$ bacteria per ml of blood. In this environment, the vegetative bacteria respond to physiological body temperature and $CO_2$ levels to transcriptionally activate genes responsible for capsule formation and toxin synthesis. Finally, massive edema and organ failure are produced as a consequence of toxin formation. Experience with the 2001 bioterrorism incident found that once the disease reaches the phase where patients show evidence of significant toxin production, treatment with antibiotics can do little to prevent a fatal outcome. Similar results were reported in animal models. Accordingly, early diagnosis and intervention prior to toxin production is essential to patient survival.

*Bacillus anthracis* can also produce cutaneous anthrax or gastrointestinal anthrax. Cutaneous or gastrointestinal anthrax may show local signs and symptoms. In some cases, cutaneous or gastrointestinal anthrax can disseminate to produce the sepsis syndrome that occurs following inhalation anthrax.

Treatment of anthrax is dependent on administration of antibiotics early in the course of disease. Successful treatment requires that the bacterium be sensitive to available antibiotics and that antibiotics be administered before large amounts of toxin are released. A delay in antibiotic treatment may substantially lessen chances for survival. If a sufficient level of toxin production occurs, there is little in the way of specific therapy that is available for treatment. Currently, bacteriological culture is the mainstay for diagnosis of anthrax. Unfortunately, a preliminary diagnosis of anthrax requires 12-24 h of culture, and definitive diagnosis requires sophisticated assays that are performed by one of the members of the Laboratory Response Network. As a consequence, there is an urgent need for diagnostic tests that will allow for early diagnosis at the point of initial patient contact.

A further complication in the treatment of anthrax is the possibility that a biowarfare strain can be engineered to resist treatment by conventional antibiotics. For example, there is a report of a *Bacillus anthracis* strain that has been engineered to resist the tetracycline and penicillin classes of antibiotics. Similarly, the *bacillus* could be engineered to produce a toxin that would evade anthrax vaccines that target the anthrax toxin.

Like many members of the genus *Bacillus*, *Bacillus anthracis* is surrounded by a capsule comprised of high molecular weight polymers of glutamic acid. In the case of *Bacillus anthracis*, the capsule is composed entirely or almost entirely of poly γ-D-glutamic acid (γDPGA). The capsule is believed to contribute to pathogenesis by preventing phagocytosis of the bacterium. This enables the microbe to replicate in blood or tissues at which time the bacterium elaborates three proteins that contribute to the pathogenesis of anthrax—namely, protective antigen, lethal factor, and edema factor.

Studies of γDPGA production during infection and an assessment of protection by anti-γDPGA antibodies have been hampered by the poor immunogenicity of this antigen, the inherent difficulty in generating monoclonal antibodies (mAbs) to weakly immunogenic antigens, and the consequent lack of immunochemical reagents. As a result, neither the extent of γDPGA production during anthrax nor the role of γDPGA as a target for active or passive immunization is known. Recent studies demonstrated that protein conjugates of γDPGA had enhanced immunogenicity in mice, highlighting the γDPGA capsule as a potential target for vaccine development (Schneerson, et al., PROC. NATL. ACAD. SCI. U.S.A., 100:8945-8950 (2003); and Rhie, et al., PROC. NATL. ACAD. SCI. U.S.A., 100:10925-10930 (2003)). However, the effectiveness of anti-γDPGA antibodies in preventing or treating anthrax in vivo has not been reported.

SUMMARY OF THE INVENTION

The present invention provides compositions and methods that are useful for the detection, prevention, or treatment of anthrax or other infectious diseases. In one aspect, the present invention provides methods useful for immunizing humans or other vertebrates against infections of Bacillus anthracis or other capsulated pathogens. The methods include administration of a capsular polypeptide of a pathogen of interest and a CD40 agonist to a vertebrate. The capsular polypeptide and the CD40 agonist are administered in such an amount or frequency that an immunoprotective response can be elicited in the vertebrate against the pathogen. In one embodiment, the vertebrate being immunized is a human who has been exposed or is at risk of exposure to Bacillus anthracis or other pathogens.

Numerous immunization regimes can be used to produce the desired immune responses. In one embodiment, the CD40 agonist is administered simultaneously with the capsular polypeptide. For instance, the capsular polypeptide and the CD40 agonist can be administered in the same pharmaceutical composition. In another embodiment, the capsular polypeptide and the CD40 agonist are administered sequentially or substantially simultaneously. In still another embodiment, the initial immunization is following by one or more booster immunizations with the capsular polypeptide. The booster immunization(s) may or may not include the CD40 agonist. In one example, the booster immunization(s) is administered at least 5 days, 10 days, 20 days, 1 month, 2 months, 3 months, 6 months, or 1 year after the initial immunization.

In yet another embodiment, the pathogen of interest is Bacillus anthracis, and the capsular polypeptide is γDPGA. The CD40 agonist can be an agonistic anti-CD40 antibody. Other agents or molecules that can bind to and activate CD40 receptors on B cells may also be used in the present invention. In one example, γDPGA is prepared from avirulent Bacillus licheniformis in a liquid medium under conditions that favor production of PGA in the D isoform. The Bacillus licheniformis PGA can be isolated in large amounts from the supernatant fluid to yield a high molecular weight product.

In still another embodiment, the capsular polypeptide is γLPGA. Bacillus anthracis can be genetically modified to produce a capsule that is composed of γLPGA. This can be achieved, for example, by taking the capsule gene from other Bacillus species that make PGA in the L isoform. Immunization with γLPGA provides effective protections against this type of genetically engineered Bacillus anthracis strains.

In a further embodiment, humans or other vertebrates are immunized with both γDPGA and γLPGA. Immunoprotective reactions against both conventional and genetically engineered Bacillus anthracis strains can therefore be produced.

In another aspect, the present invention provides antibodies specific for γDPGA, γLPGA, or other capsular polypeptides. The antibodies of the present invention can be derived from vertebrates immunized according to the present invention. These antibodies can be, without limitation, polyclonal, monoclonal, chimeric, humanized, scFv, Fv, Fab', Fab, or F(ab')$_2$.

The present invention also features hybridomas capable of producing antibodies specific for γDPGA, γLPGA, or other capsular polypeptides. In addition, the present invention provides methods for high efficiency hybridoma production. In one embodiment, the methods include boosting the immunized vertebrates shortly prior to harvesting of splenic cells for hybridoma production.

The antibodies of the present invention can be used for the diagnosis, prevention, or treatment of anthrax or other infectious diseases. In one aspect, the present invention provides methods useful for detecting pathogen infections. The methods include contacting a sample with an antibody of the present invention to detect the presence or absence of a capsular polypeptide of a pathogen of interest in the sample. An abnormally high level of the capsular polypeptide in the sample may indicate the existence or infection of the pathogen. In one embodiment, the sample being analyzed is a biological sample, such as a blood sample, a urine sample, a bodily waste sample, a skin sample, a gastrointestinal sample, a cerebrospinal fluid sample, or other body fluid or tissue samples. Environmental, food, beverage, mail, or other types of samples can also be analyzed according to the present invention.

In another embodiment, pathogen infections are detected by monitoring the levels of soluble capsular polypeptides (e.g., γDPGA or γLPGA) in blood or other body fluid samples. This method affords several significant improvements to current methods for diagnosis of anthrax or other infectious diseases. For example, the method allows for a diagnostic test that is faster than current culture conditions, easier than nucleic acid hybridization techniques, and is not dependent on the presence of viable pathogen that would not be present in the event that a patient had been treated with antibiotics. Moreover, an assay for blood or serum PGA can rapidly assess the microbial load in a patient and aid in an assessment of patient prognosis.

In yet another aspect, the present invention provides methods of using antibodies for preventing (e.g., by passive immunoprophylaxis) or treating (e.g., passive immunotherapy) anthrax or other infectious diseases. The methods include administering an effective amount of an antibody to a human or animal, where the antibody is specific for a capsular polypeptide of a pathogen of interest. The administration may be pre-exposure or post-exposure to the pathogen of interest. In one embodiment, the pathogen of interest is Bacillus anthracis, and the antibody includes an anti-γLPGA or anti-γLPGA mAb. Passive immunization with PGA antibodies targets the capsule of Bacillus anthracis, a target that is essential for the production of disease and is not amenable to weaponization by way of genetic engineering to make the bacterium resistant to the current toxin-based immunity or generation of antibiotic resistance.

In still another aspect, the present invention provides pharmaceutical compositions comprising the antibodies or vaccines of the present invention. In one embodiment, the pharmaceutical compositions include a CD40 agonist (e.g., an agonistic anti-CD40 antibody) and a pathogenic capsular polypeptide (e.g., γLPGA, γLPGA, or both).

Other features, objects, and advantages of the present invention are apparent in the detailed description that follows. It should be understood, however, that the detailed description, while indicating preferred embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are provided for illustration, not limitation.

FIG. 5A demonstrates double immunodiffusion showing reactivity of mAb F26G3 with γDPGA from *Bacillus licheniformis* ("B1 PGA"), with total γDPGA isolated from *Bacillus anthracis* ("Ba PGA (T)"), with the low molecular weight fraction of γDPGA isolated from *Bacillus anthracis* ("Ba PGA (L)"), and with the high molecular weight fraction of γDPGA isolated from *Bacillus anthracis* ("Ba PGA (H)"). The arrow identifies a weak precipitin line produced by a high molecular weight component of the total γDPGA.

FIG. 5B shows the binding of Alexa Fluor 488 conjugated mAb F26G3 (50 μg/ml) to *Bacillus anthracis* when viewed by differential interference contrast (DIC) microscopy to show quellung reaction.

FIG. 5C shows the binding of Alexa Fluor 488 conjugated mAb F26G3 (50 μg/ml) to *Bacillus anthracis* when viewed by confocal microscopy.

DETAILED DESCRIPTION OF THE INVENTION

Figure 1A:
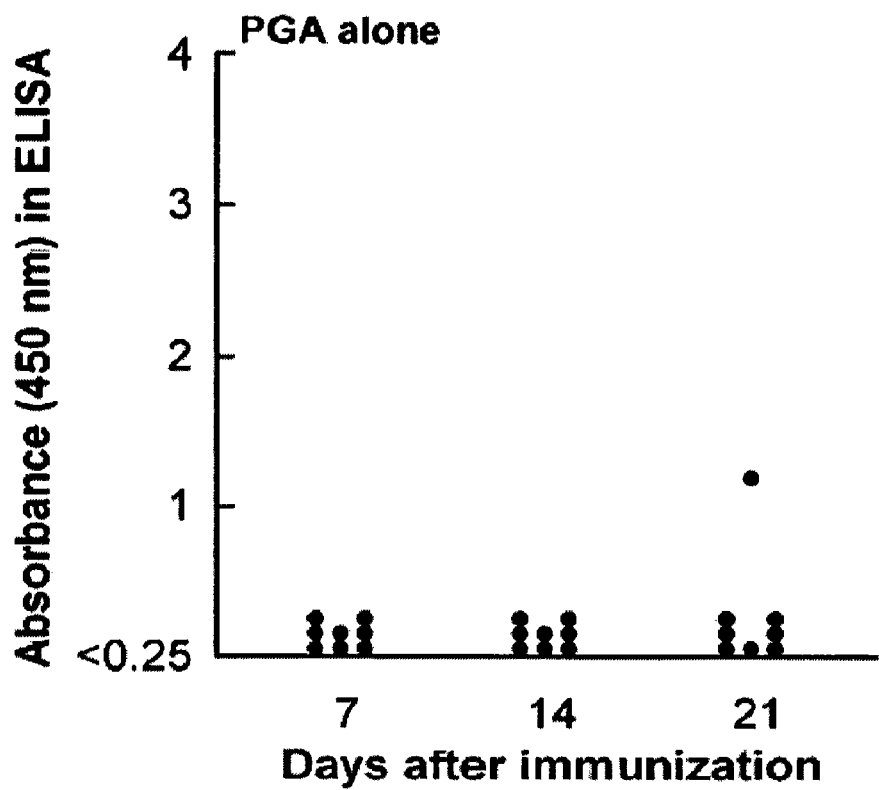
FIG. 1A demonstrates IgG antibody response to immunization of mice with PGA alone. Results are reported as the $OD_{450}$ in an IgG-specific ELISA in which microtiter plates were coated with *Bacillus licheniformis* PGA. Results are shown for sera from individual mice that were diluted 1/20.
Figure 1B:
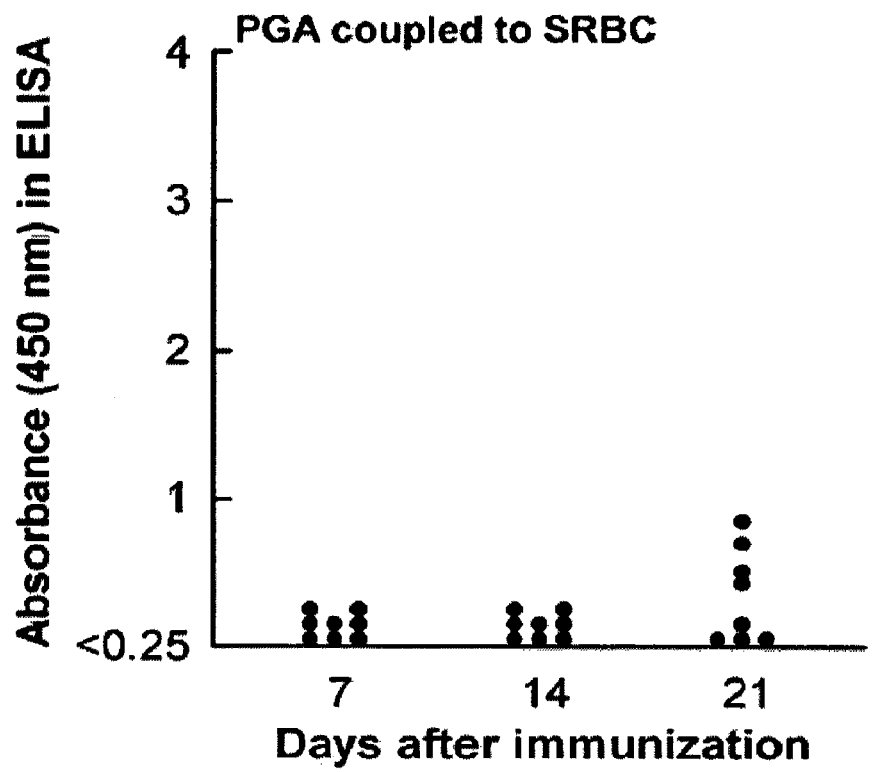
FIG. 1B shows IgG antibody response to immunization of mice with PGA coupled to sheep erythrocytes (SRBC). Results are reported as in FIG. 1A.
Figure 1C:
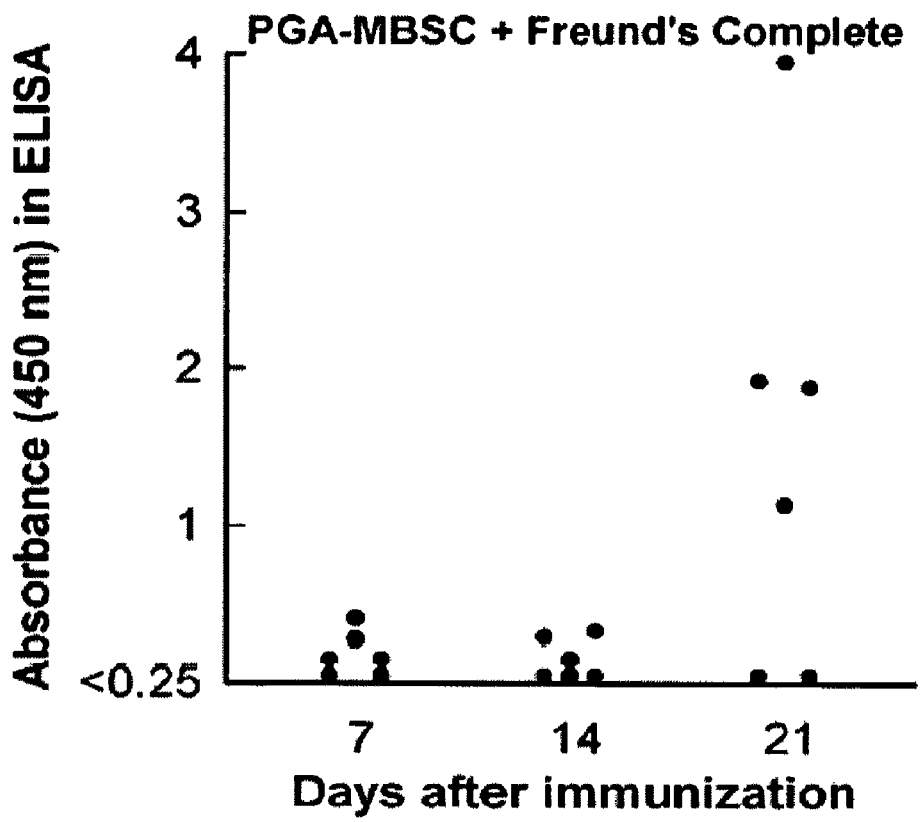
FIG. 1C depicts IgG antibody response to immunization of mice with PGA complexed with methylated bovine serum albumin (MBSA). Results are reported as in FIG. 1A.
Figure 1D:
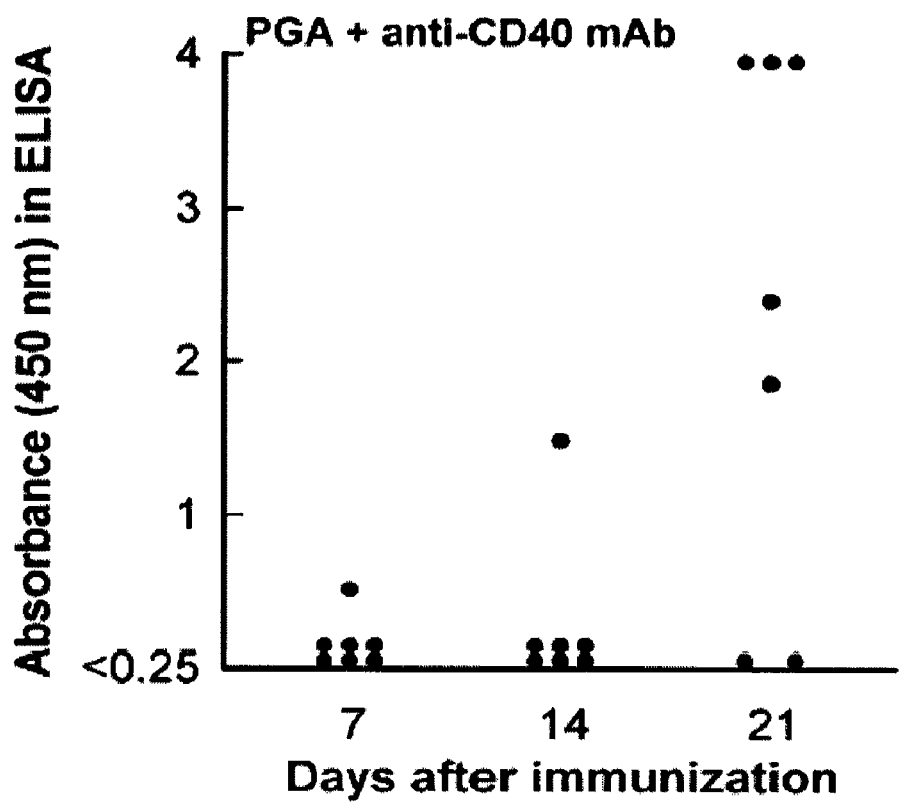
FIG. 1D shows IgG antibody response to immunization of mice with PGA in combination with CD40 agonist antibody. Results are reported as in FIG. 1A.

The present invention provides methods that are useful for immunizing humans or other vertebrates against *Bacillus anthracis* or other pathogens. The methods include administering a capsular polypeptide of a pathogen of interest (e.g., γDPGA or γLPGA) and a CD40 agonist (e.g., agonistic anti-CD40 antibodies) to a vertebrate, where the capsular polypeptide or the CD40 agonist are administered in such an amount or frequency that an immunoprotective response can be produced in the vertebrate against the pathogen. In many embodiments, the immunization regimes of the present invention include an initial administration of the capsular polypeptide and the CD40 agonist, followed by at least one booster immunization with the capsular polypeptide. The booster immunization(s) may or may not include the CD40 agonist. In many other embodiments, the immunization regimes may include only a single administration of the capsular polypeptide in combination with the CD40 agonist.

The antibodies derived from the immunized vertebrates of the present invention can be used for the diagnosis, prevention, or treatment of anthrax or other infectious diseases. In one embodiment, the level of soluble γDPGA or γLPGA in a biological sample is monitored using an anti-γDPGA or anti-γLPGA antibody, respectively. A substantial increase of soluble PGA relative to a reference level may indicate *Bacillus anthracis* infection. In another embodiment, a subject who has been exposed or is at risk of exposure to *Bacillus anthracis* is administered with an anti-PGA antibody of the present invention. This passive immunization is effective in preventing or treating anthrax.

The present invention also features vaccine formulations useful for the prevention or treatment of anthrax or other infectious diseases. In one embodiment, the vaccine formulations include a capsular polypeptide of a pathogen of interest (e.g., γDPGA or γLPGA) and a CD40 agonists (e.g., an agonistic anti-CD40 antibody). In many instances, the capsular polypeptide in a vaccine formulation of the present invention is not conjugated or fused to any other protein or carrier.

Various aspects of the present invention are described in further detail in the following sections. The use of sections is not meant to limit the invention. Each section may apply to any aspect of the invention. As used herein, the term "or" means "and/or" unless stated otherwise. Also, the use of the singular includes the plural unless stated otherwise.

I. Capsular Polypeptides

Capsular polypeptides amenable to the present invention include, but are not limited to, capsular polypeptides of bacteria, viruses, parasites, or other pathogenic microbes. In many embodiments, the capsular polypeptides are poor immunogens when used in non-conjugated forms. In one example, the capsular polypeptides comprise a significant amount of repetitive units. In another example, the capsular polypeptides are T cell independent antigens. T-cell help, during responses to protein antigens, can produce stronger humoral antibody responses and isotype switching to the IgG isotypes. T-cell help can be mediated through cognate interactions between the B-cell surface antigen, CD40, and the T cell ligand, CD40L. Without T-cell help, foreign antigens may induce only weak IgM antibody responses. In still another example, the capsular polypeptides are bacterial capsular polypeptides, such as capsular polypeptides of *Bacillus* species.

The capsular polypeptides used in the present invention may or may not be conjugated with carriers. The present invention demonstrates that administration of a non-conjugated capsular polypeptide in combination with a CD40 agonist is sufficient to induce a robust humoral antibody response against the capsular polypeptide. Therefore, the present invention provides an effective and inexpensive alternative for generating antibodies specific for poorly immunogenic capsular polypeptides.

The present invention does not preclude the use of capsular protein conjugates. Covalent linkage to immunogenic carriers can significantly increase the immunogenicity of capsular polypeptides. Any immunogenic carrier can be employed in the present invention. A capsular polypeptide can be conjugated to a carrier either covalently, non-covalently, or both. Examples of suitable capsular polypeptide conjugates include, but are not limited to, those described in Schneerson, et al., supra, and Rhie, et al., supra, which are incorporated herein by reference.

In one embodiment, the capsular polypeptides of the present invention are poly γ-D-glutamic acid (γDPGA). γDPGA is the primary component of the capsule of *Bacillus anthracis*. γDPGA can be prepared using a variety of methods. For instance, γDPGA can be prepared from *Bacillus anthracis* using the methods described in Schneerson, et al., supra. For another instance, γDPGA can be isolated from *Bacillus licheniformis* which is grown under conditions that favor the production of γPGA in the D conformation. See, for example, Thorne, et al., J. BIOL. CHEM., 233:1109-1112 (1958) and Rhie, et al., supra. A comparison of γDPGA produced by *Bacillus licheniformis* and that of *Bacillus anthracis* is provided in Example 1. The use of *Bacillus licheniformis* PGA provides several advantages. First, the cultural conditions for growth of *Bacillus licheniformis* can be modified to experimentally control the percentage of the D- or L-isoforms. This may be advantageous in formulation of a robust immunization strategy aimed at generation of a library of mAbs having distinct epitope specificities. Second, reports in the literature suggest that PGA produced by *Bacillus licheniformis* has a higher molecular weight than PGA from *Bacillus anthracis*. PGA from *Bacillus licheniformis* has been reported to have a weight-average molecular weight ranging between $8.4 \times 10^4$ and $1.2 \times 10^6$. In contrast, reports of the molecular weight of the *Bacillus anthracis* PGA range from $3.3 \times 10^4$ to $7.5 \times 10^4$ to $3.4 \times 10^5$. In many cases, the immunogenicity of a capsular antigen may increase with its molecular weight. Third, the use of *Bacillus licheniformis* can avoid working with a dangerous agent. This also allows for isolation of PGA without having to kill the bacterium by means that might have altered structure or immunogenicity, e.g., autoclaving or use of chemical agents. γLPGA can also be prepared using chemical synthesis, as appreciated by those skilled in the art.

In another embodiment, the capsular polypeptides of the present invention are poly γ-L-glutamic acid (γLPGA). *Bacillus anthracis* can be weaponized or otherwise modified for production of PGA in the L isoform to effect evasion of antibodies specific for the D isoform. Immunization with γLPGA can effectively protect humans or other vertebrates from this type of weaponized *Bacillus anthracis*. γLPGA is the primary component of the capsules of many *Bacillus* species. Methods for extracting γLPGA from these *Bacillus* species are well known in the art.

The capsular polypeptides of the present invention can also be provided in other forms, such as bacterial extracts, partial purifications, or killed or attenuated bacteria. In one example, crude extracts of *Bacillus licheniformis* or chemically killed *Bacillus anthracis* are used, in combination with CD40 agonists, to elicit immunoprotective reactions against *Bacillus anthracis*.

II. CD40 Agonists

CD40 agonists activate CD40 receptors either directly or indirectly. Agents that directly stimulate CD40 receptors include agnostic anti-CD40 antibodies. These antibodies may be polyclonal, monoclonal, chimeric, or humanized. They may also be scFv, Fv, Fab', Fab, F(ab')$_2$, or other antigen-binding regions or fragments of anti-CD40 antibodies. Examples of agnostic anti-CD40 antibodies include, but are not limited to, those described in Hixon, et al., BIOL. BLOOD MARROW TRANSPLANT, 7:136-43 (2001) (e.g., FGK115 MAb), U.S. Pat. No. 6,482,411 (e.g., G28-5, mAb89, EA-5, and S2C6 MAb), and Dullforce, et al., NAT. MED., 4:88-91 (1998), which are incorporated herein by reference.

CD40 agonists that are useful for the present invention may also include membrane, soluble, or recombinant CD40L proteins. In addition, they may be fusion proteins including one or more copies of CD40L, or functional fragments of CD40L proteins. Other agents or molecules that bind to and activate CD40 receptors on B cells may also be used in the present invention.

CD40 agonists may be selected to match to the species of the subject that is being treated. For instance, humanized anti-CD40 antibodies or human CD40L proteins can be used for administration to humans. In some embodiments, CD40 agonists that do not match to the species being treated can also be used, provided that the CD agonists are capable of stimulating CD40 receptors on the B cells in that species.

Moreover, the present invention also features the use of agents that indirectly stimulate or activate CD40 receptors. These indirect CD40 agonists include, without limitation, accessory signaling molecules, co-stimulators or the like, and agents that remove, inactivate or downregulate inhibitors of the CD40 signaling process. The indirect CD40 agonists also include molecules that stimulate or upregulate the expression of CD40 receptors on B cells. These molecules increase the amount of CD40 receptors on the cell surface, thereby amplifying the effect of the natural biological ligand counterpart or exogenously added CD40 ligands or antibodies.

III. Pharmaceutical Compositions and Immunization Regimes

Any immunization regime known in the art may be used by the present invention to effectively immunize humans or other vertebrates (e.g., buffalo, cattle, sheep, goat, swine, camel, chicken, duck, or other domesticated animals) against *Bacillus anthracis* or other pathogens. Each of these immunization regimes includes administration of a capsular polypeptide and a CD40 agonist to a subject of interest. In many embodiments, the capsular polypeptides and CD40 agonists are administered in pharmaceutical compositions. The pharmaceutical compositions of the present invention (including vaccine formulations) typically include a pharmaceutically acceptable carrier. Examples of pharmaceutically acceptable carriers include, but are not limited to, solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic or absorption delaying agents, and the like, that are compatible with pharmaceutical administration.

The pharmaceutical compositions of the present invention may be formulated to be compatible with their intended routes of administration. Suitable routes of administration include, but are not limited to, parenteral, enteral, and topical administration. Examples of routes of administration include intracutaneous, epicutaneous, inhalative, oral, rectal, intravenous, intraarterial, intramuscular, subcutaneous, intradermal, transdermal, or transmucosal administration. A pharmaceutical composition of the present invention can also be administered by gastric feeding or duodenal feeding tubes.

Examples of suitable materials for use in immunization are described in REMINGTON'S PHARMACEUTICAL SCIENCES (pp. 1324-1341, Mack Publishing Co., Easton, Pa. 1980). For instance, solutions or suspensions suitable for parenteral, intradermal, or subcutaneous administration can include, without limitation, the following components: a sterile diluent such as water, saline solution, fixed oils, polyethylene glycols, glycerine, propylene glycol or other synthetic solvents; antibacterial or antifungal agents such as parabens, chlorobutanol, phenol, ascorbic acid, thimerosal, benzyl alcohol and the like; antioxidants such as ascorbic acid or sodium bisulfate; chelating agents such as ethylenediaminetetraacetic acid; buffers such as acetates, citrates or phosphates; and agents for the adjustment of tonicity such as sodium chloride or dextrose. pH can be adjusted with acids or bases, such as hydrochloric acid or sodium hydroxide.

In one embodiment, the pharmaceutical compositions of the present invention are injectable. These compositions can include, without limitation, sterile aqueous solutions or dispersions, or sterile powders for the extemporaneous preparation of injectable solutions or dispersions. For intravenous administration, suitable carriers include, without limitation, phosphate buffered saline (PBS), bacteriostatic water, or Cremophor EL™ (BASF, Parsippany, N.J.). In many cases, the injectable compositions are fluid to the extent that easy syringability exists. The proper fluidity can be maintained, for example, by using a surfactant or a coating such as lecithin, or by maintaining the requited particle size in the case of dispersion. Prolonged absorption of an injectable composition can be achieved by including in the composition an agent which can delay absorption, for example, aluminum monostearate or gelatin.

The injectable compositions of the present invention can be prepared, for instance, by incorporating the active ingredients (e.g., capsular polypeptides or CD40 agonists) in the required amount in an appropriate solvent, followed by filtered sterilization. The injectable compositions can also be prepared by incorporating the active ingredients into a sterile vehicle which contains a dispersion medium. In one embodiment, powders of the active ingredients, plus any additional desired ingredient, are prepared by vacuum drying or freeze-drying. The sterile powders are then reconstituted to form the injectable compositions of the present invention.

In another embodiment, the pharmaceutical compositions of the present invention can be delivered orally. This type of compositions generally includes an inert diluent or an edible carrier. In many cases, the active ingredients are incorporated with excipients and used in the form of tablets, troches, or capsules. These tablets, troches, or capsules can include any of the following compounds or the equivalents thereof: a binder such as microcrystalline cellulose, gum tragacanth or gelatin; an excipient such as starch or lactose; a disintegrating agent such as alginic acid, Primogel or corn starch; a lubricant such as magnesium stearate or Stertes; a glidant such as colloidal silicon dioxide; a sweetening agent such as sucrose or saccharin; or a flavoring agent such as peppermint, methyl salicylate or orange flavoring.

In yet another embodiment, the pharmaceutical compositions of the present invention are inhalative. These compositions can be delivered in the form of an aerosol spray from a pressured container or dispenser which contains a suitable propellant (such as carbon dioxide) or nebulizer.

In a further embodiment, the pharmaceutical compositions of the present invention can be delivered via transmucosal or transdermal routes. Penetrants appropriate to the barrier to be permeated are frequently used in this type of formulation. Suitable penetrants include, but are not limited to, detergents, bile salts, or fusidic acid derivatives. Transmucosal administration can also be accomplished by using nasal sprays or suppositories. For transdermal administration, the active ingredients can be formulated into ointments, salves, gels, or creams.

In still yet another embodiment, the pharmaceutical compositions of the present invention are prepared with carriers that will protect the active ingredients from being rapidly eliminated from the body. For instance, the pharmaceutical compositions can employ a controlled release formulation, an implant, or a microencapsulated delivery system. Biodegradable, biocompatible polymers can also be used, such as ethylene vinyl acetate, polyanhydrides, polyglycolic acid, collagen, polyorthoesters, and polylactic acid.

The pharmaceutical compositions of the present invention can be administered in a manner compatible with the dosage formulation, and in such an amount as will be immunogenic or therapeutically effective. The quantity to be administered depends on the subject to be treated, including, without limitation, the capacity of the individual's immune system to synthesize antibodies, the degree of protection desired, and the potency or half-life of the composition to be administered. Precise amounts of active ingredients depend on the judgment of the practitioner and can be determined using methods that are routine in the art. Regimens for initial administration and booster shots are also variable. In many embodiments, the immunization regimes include an initial administration followed by subsequent inoculations or other administrations.

Capsular polypeptides or CD40 agonists can be administered in one dose or multiple doses. The doses can be administered at intervals such as once daily, once weekly, or once monthly. In one embodiment, each dose includes about 0.1 µg-100 mg, 1-10 mg, 10 µg-1 mg, or 100 µg-500 µg of capsular polypeptides or CD40 agonists. Dosages below 0.1 µg or above 100 mg can also be used. The volume of each dose can range, for example, between 0.1 ml and 5 ml, between 0.1 ml and 1 ml, or between 0.2 ml and 0.5 ml. In another embodiment, capsular polypeptides or CD40 agonists are administered as a bolus dose to maximize their circulating levels, followed by booster injections or continuous infusions of capsular polypeptides.

In yet another embodiment, capsular polypeptides or CD40 agonists are administered with an adjuvant. Adjuvants enhance immunogenicity but are not necessarily immunogenic themselves. Suitable adjuvants are well known to those skilled in the art and include, without limitation, aluminum phosphate, saponins, plutonic polymers with mineral oil, killed mycobacteria in mineral oil, Freund's complete adjuvant, bacterial products, such as muramyl dipeptide (MDP) and lipopolysaccharide (LPS), as well as monophoryl lipid A, QS 21, polyphosphazene, or the derivatives thereof. Some of these adjuvants are toxic or may cause undesirable sideeffects. Caution should be used when selecting proper adjuvants.

In still yet another embodiment, the immunization regimes of the present invention include administration of PGA (e.g., γDPGA, γLPGA, or both) and an agonistic anti-CD40 antibody. The administrations of PGA and the anti-CD40 antibody can be sequential or substantially simultaneous. In one example, PGA and the anti-CD40 antibody are administered in the same pharmaceutical composition. In another example, the administration of PGA is separated from that of the antiCD40 antibody by no more than 1, 2, 3, 4, 5, 10, or 24 hours. The administration of PGA can be either before or after that of the anti-CD40 antibody.

In another embodiment, the initial administration of PGA and the anti-CD40 antibody is followed by one or more booster immunizations with PGA. The interval between the initial immunization and the booster immunization(s) can vary considerably. For instance, the interval can be at least 5 days, 10 days, 20 days, 30 days, 1 week, 2 weeks, 3 weeks, 4 weeks, 1 month, 2 months, 3 months, 6 months, 1 year, or longer. In still yet another embodiment, the immunization regimes include only an initial administration of PGA and the anti-CD40 antibody without any further booster injections or immunizations. The present invention demonstrates that a single administration of capsular polypeptides in combination with CD40 agonists can generate an immunoprotective antibody response against pathogens that bear the capsular polypeptides.

IV. Production of Antibodies

The present invention provides antibodies specific for γDPGA, γLPGA, or other capsular polypeptides. These antibodies can be used for the diagnosis, prevention, or treatment of anthrax or other pathogen infections. In many embodiments, the antibodies of the present invention can bind to the respective capsular polypeptides with a binding affinity of at least $10^5$ $M^{-1}$, $10^6$ $M^{-1}$, $10^7$ $M^{-1}$, $10^8$ $M^{-1}$, or higher. The antibodies can be polyclonal, monoclonal, chimeric, humanized, scFv, Fv, Fab', Fab, F(ab')$_2$, or other types of antigen-binding molecules or fragments. The antibodies can be derived from any immunized vertebrate of the present invention, such as mice, rats, rabbits, chickens, sheep, horses, or humans. Methods for isolating and selecting antibodies from immunized subjects are well known in the art.

In many cases, humanized antibodies are employed for clinical use in human subjects. Humanized antibodies comprise both human and non-human sequences. In one embodiment, the humanized antibodies of the present invention include human immunoglobulins (recipient antibody) in which residues forming the complementary determining regions (CDRs) are replaced by residues from CDRs of nonhuman species (donor antibody). These non-human CDR sequences may have the desired antigen-binding specificity and affinity. In some examples, the Fv framework residues of a human immunoglobulin are replaced by corresponding non-human residues, and the substantial portion of the Fc region retains the human sequence. Humanized antibodies may also include residues that are not found in either the recipient or donor antibody.

Humanized antibodies can be prepared using standard recombinant DNA techniques. In one embodiment, humanized antibodies are produced using transgenic mice. These mice are incapable of expressing endogenous immunoglobulin heavy and light chain genes, but can express human heavy and light chain genes. The transgenic mice are immunized with a selected antigen, e.g., γDPGA or γLPGA, in combination with a CD40 agonist. Monoclonal antibodies directed to the antigen can be selected using the conventional hybridoma technology. The human immunoglobulin transgenes harbored in the transgenic mice rearrange during B cell differentiation, followed by class switching and somatic mutation.

In another embodiment, humanized antibodies are generated using a technique referred to as "guided selection." In this approach, a selected non-human monoclonal antibody, e.g., a murine antibody, is used to guide the selection of a humanized antibody that recognizes the same epitope.

Furthermore, the present invention provides hybridomas capable of producing monoclonal antibodies specific for γDPGA, γLPGA, or other capsular polypeptides. Various methods are available for making hybridomas. In one example, a non-human vertebrate, such as a mouse, rabbit, sheep, or another mammal, is immunized using an immunization regime of the present invention. For instance, the non-human vertebrate can be initially immunized with a composition including a capsular polypeptide of interest and a CD40 agonist. The initial immunization may be followed by one or more booster injections of the capsular polypeptide. In many embodiments, a booster injection is performed shortly prior to the isolation of splenocytes from the immunized vertebrate. The isolated splenocytes are fused with an immortalized cell line to form hybridomas. Hybridomas capable of producing antibodies specific for the capsular polypeptide of interest can be identified using a variety of immunoassays, such as enzyme linked immunosorbent assays (ELISAs).

The hybridoma production methods of the present invention represent a general platform technology that is useful for rapid production of high affinity monoclonal antibodies for weakly immunogenic antigens. In many embodiments, the weakly immunogenic antigens are T-independent antigens. T-independent antigens amenable to the present invention include, but are not limited to, capsular polysaccharides of a variety of pathogens. Examples of these pathogens include, but are not limited to, pathogenic yeast such as *Cryptococcus*, gram-positive bacteria, such as Streptococci, Staphylococci, Enterococci, *Corynebacterium, Listeria, Erysipelothrix* and *Clostridium*, and gram-negative bacteria, such as *Haemophi-*

*lus, Neisseria* and *Escherichia*. Specific examples include, without limitation, *Cryptococcus neoformans, Staphylococcus aureus,* Group B *Streptococcus* (e.g., *Streptococcus agalactiae*), *Streptococcus pneumoniae, Haemophilus influenzae, Neisseria meningitidis,* and *Escherichia coli*.

These pathogens often cause serious human infections and morbidity throughout the world. For instance, *Staphylococcus aureus* is a leading cause of soft tissue infections. It can cause conditions such as pneumonia, meningitis, skin conditions (e.g. acne, boils or cellulites), arthritis, osteomyelitis, endocarditis, urinary tract infections, and toxic shock syndrome. Systemic group B streptococcal infections during the first two months of life affect approximately three out of every 1,000 births. These infections cause symptoms of congenital pneumonia, sepsis, and meningitis. Monoclonal antibodies against the capsular antigens (e.g., capsular polysaccharides) of these pathogens provide powerful tools for diagnosis, prevention or treatment of the infections caused by these pathogens. Pathogenic capsular polysaccharides can be prepared in any form by using any method known in the art.

In one embodiment, the capsular polysaccharide of a pathogen, in combination with a CD40 agonist (e.g., an agnostic anti-CD40 antibody), is administered to a non-human mammal (e.g., a mouse) to elicit an antibody response to the capsular polysaccharide. The administrations of the capsular polysaccharide and the CD40 agonist can be simultaneous or sequential. The CD40 agonist can significantly accelerate the antibody response to the capsular polysaccharide. A booster immunization with the capsular polysaccharide can be administered shortly before isolation of splenocytes for hybridoma production. In one example, the booster immunization is administered to the non-human mammal at about 4, 6, 8, 10, 15, 20, 25, 30 or more days after the initial immunization. The splenocytes can be isolated from the non-human mammal at 1, 2, 3, 4, 5, 6, 7, 8, 9, 10 or more days after the booster immunization.

Polyclonal antibodies specific for γDPGA, γLPGA, or other capsular polypeptides or antigens can also be prepared using the immunization regimes of the present invention. Antibody titers in an immunized subject can be monitored over time using standard techniques, such as ELISAs, radioimmunoassays (RIAs), or Western blots.

V. Prevention and Treatment of Anthrax or Other Diseases

The present invention provides prophylactic or therapeutic vaccines for immunizing humans or animals against anthrax or other infectious diseases. In one embodiment, the vaccine compositions of the present invention include an unconjugated capsular polypeptide and a CD40 agonist. In another embodiment, the vaccine compositions include only an unconjugated capsular polypeptide as the active ingredient. The immunogenicity of the unconjugated capsular polypeptide can be enhanced by administering a CD40 agonist before, during, or after the administration of the capsular polypeptide. The vaccine compositions of the present invention can be administered to a subject of interest according to any immunization regime of the present invention. In many instances, antibodies thus produced can confer sufficient immunoprotection against pathogens that bear the capsular polypeptides being administered.

In one example, a vaccine composition including PGA (e.g., γDPGA, γLPGA, or both) and an agonistic anti-CD40 antibody is administered to a human who has been exposed or is at risk of exposure to *Bacillus anthracis* or *Bacillus anthracis* spores. Humans that can be vaccinated according to the present invention include, but are not limited to, military or security force personals, mail handlers, clinicians or laboratorians who may have close contact with *Bacillus anthracis* spores, civilians or industrial workers who could be exposed to infected animals or their products, newborns or children, elderlies, or the public at large.

In many embodiments, the immunization regimes of the present invention produce rapid antibody responses after the initial administration of a capsular polypeptide and a CD40 agonist. In one example, immunoprotective antibody response can be induced less than 4 days, 5 days, 6 days, 7, days, 8 days, 9 days, or 10 days after the initial immunization. This allows for post-exposure immunization for preventing the development of serious disease conditions. In contrast, conventional toxin-based vaccines or the protein-conjugate vaccines may require weeks or months before an effective immune response can be produced.

The present invention also provides antibodies that are useful for the prevention or treatment of anthrax or other infectious diseases. In many infectious diseases, passive immunization with antibodies against the capsule of the disease-causing pathogen may prevent, alleviate, or cure the disease.

The antibodies of the present invention can be administered via a variety of routes. Desirable prophylactic or therapeutic dosages for the antibodies can range, for example, from 1 mg to 100 mg, from 10 mg to 90 mg, from 20 mg to 80 mg, from 30 mg to 70 mg, or from 40 mg to 60 mg. Dosages below 1 mg or above 100 mg can also be used. Dosage schedules can be adjusted based on, for example, the affinity of the antibody for its target, the half-life of the antibody, and the severity of the patient's condition. The amounts required for short-term protection, long-term protection, pre-exposure protection, or post-exposure protection may vary. In many cases, efficacy is greatest when the antibodies are administered early in the incubation period. In many other cases, the antibodies are administered at a later stage of the infection, but still can significantly attenuate the clinical expression or syndrome of the disease.

Toxicity and therapeutic efficacy of an antibody of the present invention can be determined by standard pharmaceutical procedures in cell culture or experimental animal models. For instance, the $LD_{50}$ (the dose lethal to 50% of the population) and the $ED_{50}$ (the dose therapeutically effective in 50% of the population) can be determined. The dose ratio between toxic and therapeutic effects is the therapeutic index, and can be expressed as the ratio $LD_{50}/ED_{50}$. Antibodies that exhibit large therapeutic indices can be selected.

The data obtained from cell culture assays or animal studies can be used to formulate a range of dosages for use in humans. The dosage may lie, without limitation, within a range of circulating concentrations that exhibit an $ED_{50}$ with little or no toxicity. The dosage may vary within this range depending upon the dosage form employed and the route of administration utilized. For any antibody used according to the present invention, a prophylactic or therapeutically effective dose can be estimated initially from cell culture assays. A dose may be formulated in animal models to achieve a circulating plasma concentration range that exhibits an $IC_{50}$ (i.e., the concentration of an antibody which achieves a half-maximal prevention or inhibition of symptoms) as determined by cell culture assays. In addition, the effects of any particular dosage can be monitored by other bioassays.

The dosage regimen for administration of a composition of the present invention can be determined by the attending physician based on various factors such as the type of pathogen, the site of pathology, the severity of disease, the patient's age, sex, and diet, the severity of any inflammation, time of administration and other clinical factors. In one embodiment, systemic or injectable administration can be initiated at a dose which is minimally effective, and the dose will be increased over a pre-selected time course until a positive effect is observed. Subsequently, incremental increases in dosage will be made limiting to levels that produce a corresponding increase in effect while taking into account any adverse affects that may appear. The addition of other known factors to a final composition may also affect the dosage. Progress can be monitored by periodic assessment of disease progression using standard methods.

In one embodiment, the antibodies of the present invention are coupled with other therapeutic agents. The antibodies can guide the attached therapeutic agents to the target pathogens. A direct coupling between an agent and an antibody is possible when each possesses a substituent capable of reacting with the other. For example, a nucleophilic group, such as an amino or sulfhydryl group, may be capable of reacting with a carbonyl-containing group, such as an anhydride or an acid halide, or with an alkyl group. Alternatively, an antibody can be coupled to another therapeutic agent via a linker group. A linker group can function as a spacer to distance an antibody from the agent in order to avoid interference with binding capabilities. A linker group can also serve to increase the chemical reactivity of a substituent on the agent or antibody, and thus increase the coupling efficiency. A variety of bifunctional or polyfunctional reagents can be employed as the linker groups. Coupling may be effected, for example, through amino groups, carboxyl groups, sulfhydryl groups, or oxidized carbohydrate residues.

In another embodiment, the antibodies of the present invention are used with other antibiotics or therapies for the prevention or treatment of anthrax or other diseases.

In yet another embodiment, the antibodies of the present invention are monoclonal antibodies specific for the capsular polysaccharides of *Staphylococcus aureus* or other pathogens. Passive immunization with these antibodies can effectively protect humans or other animals from infections of these pathogens.

VI. Detection of Anthrax or Other Diseases

The present invention further features methods that are useful for detecting *Bacillus anthracis* or other pathogen infections. Many pathogens, such as *Bacillus anthracis*, can shed a significant amount of their capsular antigens during infections. Therefore, the infection status can be evaluated by detecting the level of shed capsular antigens in a biological sample of a subject of interest. The detection can be either quantitative or qualitative. In many instances, the level of shed capsular antigens is also indicative of the progression of the infection.

In one embodiment, the appearance of soluble γDPGA (or γLPGA for engineered *Bacillus anthracis* strains) in serum coincides with the emergence of *Bacillus anthracis* bacteremia. Accordingly, *Bacillus anthracis* infection can be detected by comparing the level of soluble γDPGA (or γLPGA for certain genetically engineered strains) in a blood sample from a subject of interest to a reference level of γDPGA (or γLPGA). The blood sample can be, without limitation, a whole blood sample or a serum sample. Other biological samples can also be used for detecting the levels of PGA or other shed capsular proteins or antigens. These biological samples include, but are not limited to, urine samples, bodily waste samples, skin samples, gastrointestinal samples, cerebrospinal fluid samples, or other body fluid or tissue samples. Capsular polypeptides in environmental, food, beverage, mail, or other types of samples can also be assessed using the antibodies of the present invention to determine the presence or absence of *Bacillus anthracis* or other capsulated pathogens.

In many embodiments, the reference γDPGA (or γLPGA) level is an average level of soluble γDPGA (or γLPGA) in blood samples from reference subjects who have not been infected by or exposed to *Bacillus anthracis*. The reference PGA level and the PGA level being compared can be determined using the same or comparable methods. In many other embodiments, the reference γDPGA (or γLPGA) level is an average level of soluble γDPGA (or γLPGA) in blood samples from reference subjects who are infected by *Bacillus anthracis*. The reference subjects may be at the same infection or disease stage. The reference subjects may also be selected from different infection or disease stages.

In one example, the average PGA level in blood samples from *Bacillus anthracis*-free subjects is considered negligible. Thus, a detectable level of soluble PGA in a blood sample from a subject of interest is suggestive of the infection of *Bacillus anthracis*.

Numerous assay formats are available for detecting soluble γDPGA, γLPGA, or other capsular antigens. In many embodiments, immunoassays are employed. Suitable immunoassays for the present invention can be competitive or non-competitive. They can be in a direct or indirect format. They can run in either the forward, reverse, or simultaneous modes. Examples of suitable immunoassay formats include, but are not limited to, latex or other particle agglutination, electrochemiluminescence, ELISAs, RIAs, sandwich or immunometric assays, time-resolved fluorescence, lateral flow assays, fluorescence polarization, flow cytometry, immunohistochemical assays, Western blots, and proteomic chips. Those of skill in the art will know, or can readily discern, other suitable immunoassay formats without undue experimentation.

Any antibody of the present invention can be used in the immunoassays. The antibodies can be used in liquid phase or bound to a solid phase carrier. Many solid carriers are suited for this purpose. Examples of these carriers include, but are not limited to, glass, polystyrene, polypropylene, polyethylene, dextran, nylon, amylases, natural and modified celluloses, polyacrylamides, agaroses, or magnetite. The nature of the carrier can be either soluble or insoluble.

In one embodiment, antibodies are bound to solid phase carriers by adsorption from an aqueous medium, although other modes of affixation, such as covalent coupling or other well known means of affixation to the solid matrix can be used. Antibody molecules can be bound to a support before forming an immunocomplex with antigen. The immunocomplex can also be formed prior to binding the complex to the solid support. Non-specific protein binding sites on the surface of the solid phase support can be blocked. In one example, after adsorption of solid phase-bound antibodies, an aqueous solution of a protein free from interference with the assay such as bovine, horse, or other serum albumin can be admixed with the solid phase to adsorb the admixed protein onto the surface of the antibody-containing solid support at protein binding sites on the surface that are not occupied by antibody molecules.

Methods capable of detecting capsular antigens without using antibodies can also be used in the present invention. These methods include, but are not limited to, two-dimensional gel electrophoresis, mass spectrometry, or other high-throughput polypeptide sequencing or identification methods. In addition, capsular antigens can be detected using in vivo diagnosis methods. For instance, a detectably labeled antibody can be administered to a subject of interest in a diagnostically effective dose. The concentration of the detectably labeled antibody should be sufficient such that the binding to a capsular antigen of interest is detectable compared to the background.

Detection can be facilitated by coupling the antibody to a detectable substance. Examples of detectable substances include, without limitation, enzymes, prosthetic groups, fluorescent materials, luminescent materials, bioluminescent materials, radioactive materials, particulate materials, and colloidal metals. Examples of suitable enzymes include horseradish peroxidase, alkaline phosphatase, galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. Examples of a luminescent material include luminal. Examples of bioluminescent materials include luciferase, luciferin, and aequorin. Examples of suitable radioactive material include $^{125}I$, $^{131}I$, $^{35}S$, and $^{3}H$.

Another labeling technique which may result in greater sensitivity includes coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

The materials for use in the assays of the present invention can be included in a kit. The kit can comprise a carrier means being compartmentalized to receive in close confinement one or more container means such as vials, tubes, or the like, each of the container means comprising one of the elements to be used in a method of the present invention. For example, one of the container means can comprise an anti-PGA mAb of the present invention which may be either labeled or unlabeled. Unlabeled antibodies can be used in combination with other labeled antibodies (second antibodies) that are reactive with the unlabeled antibodies. In one example, the second antibodies are antibodies specific for the immunoglobulin constant regions. In another example, the anti-PGA mAb is in a soluble or lyophilized form in a container, either alone or in conjunction with additional antibodies (e.g., a secondary antibody).

The kit can also have containers containing buffers (e.g., Tris, phosphate, or carbonate), stabilizing agents (e.g., polysaccharide or the like), biocides, inert proteins (e.g., serum albumin), or reporter-means (e.g., a biotin-binding protein, such as avidin or streptavidin, which is bound to a reporter molecule, such as an enzymatic or fluorescent label). In addition, the kit can include reagents for conducting positive or negative controls. Instructions on how to use the kit can also be included.

It should be understood that the above-described embodiments and the following examples are given by way of illustration, not limitation. Various changes and modifications within the scope of the present invention will become apparent to those skilled in the art from the present description.

EXAMPLES

Example 1

Bacterial Strains, Bacterial Culture and Isolation of Poly γ-D-Glutamic Acid (γDPGA)

*Bacillus licheniformis* strain 9945 was obtained from the American Type Culture Collection. *Bacillus anthracis* Pasteur strain is maintained by the Nevada State Health Laboratory and was originally obtained from the Centers for Disease Control. *Bacillus anthracis* Ames strain was obtained from the US Army Medical Research Institute of Infectious Diseases, Frederick, MD.

*Bacillus licheniformis* was grown for 60 h on a gyratory shaker (250 rpm) at 37° C. on Medium E that contained 2 mM $MnCl_2.4H_2O$ to stimulate increased production of γPGA in the D isomer. Sodium acetate crystals and glacial acetic acid were added to final concentrations of 10% and 1%, respectively. The bacterial cells were removed by centrifugation followed by filtration, and the PGA was precipitated from the medium with two volumes of ethanol. The precipitate was resolubilized in sodium acetate buffer (10% sodium acetate crystals and 1% glacial acetic acid) and reprecipitated with ethanol. The precipitate was washed with absolute ethanol and acetone and then dried. Amino acid analysis showed the presence of only glutamic acid. A phenol-sulfuric acid test for carbohydrate was negative. An acid hydrolysate exhibited a specific optical rotation (about −25.2°), indicating that approximately 84% of the glutamic acid was in the D isoform.

A comparison of the properties of *Bacillus licheniformis* PGA produced under the above-described conditions with the published properties of *Bacillus anthracis* PGA is provided in Table 1.

TABLE 1

Comparison of the Composition of *Bacillus licheniformis* PGA with that of *Bacillus anthracis* PGA

| Property | *Bacillus licheniformis* PGA | *Bacillus anthracis* PGA[a] |
|---|---|---|
| Glutamic acid content | ≧99.9% | ≧99.0% |
| Other amino acids | ≦0.1% | ≦0.5% |
| Hexose content | ≦0.1% | ≦0.5% |
| Specific optical rotation of hydrolysate | −25° | −29.8° |

[a]Properties of *Bacillus anthracis* from Goodman and Nitecki, BIOCHEM., 5: 657-665 (1966).

*Bacillus licheniformis* was also grown in Medium E that contained 0.15 μM $MnCl_2.4H_2O$ to increase production of PGA in the L isoform. Capsulated bacteria grown in this manner were used to assess mAb binding to cells having capsules of γLPGA.

*Bacillus anthracis* γDPGA was isolated from cultures of the Pasteur strain that were grown on a dialysate of brain heart infusion broth (Difco) for 24 h on a gyratory shaker (175 rpm) at 37° C. in 15% $CO_2$. Formaldehyde was added to a final concentration of 2% for 24 h at 23° C. Non-viability of the culture was confirmed by plating on nutrient agar (Difco). γDPGA was isolated from the supernatant fluid of *Bacillus anthracis* broth cultures as described above for γDPGA from *Bacillus licheniformis*.

Example 2

Immunization of Mice to Produce Anti-γDPGA Antibodies

An initial experiment evaluated four immunization protocols. First, mice were immunized intraperitoneally (IP) with 2 μg γDPGA alone. Second, mice were immunized intravenously with sheep erythrocytes (SRBC) that had been coated with γDPGA by use of a chromium chloride procedure. This procedure had been successfully used for immunization of mice with the capsular polysaccharide of the pathogenic yeast *Cryptococcus neoformans*. Third, mice were immunized IP with a complex of γDPGA and methylated bovine serum (MBSA) in Freund's complete adjuvant. Finally, mice were immunized by intraperitoneal injection of 2 µg γDPGA in combination with a murine agonist CD40 mAb (FGK115) (500 µg).

The results (FIGS. 1A, 1B, 1C, and 1D) showed little or no response to immunization with γDPGA alone or γDPGA coupled to SRBC. The absence of an immune response to γDPGA coupled to SRBC suggests that the immune response to γDPGA is not predictable on the basis of procedures that have produced an immune response to other T-independent antigens, e.g., the capsular polysaccharide of *Cryptococcus neoformans*. Immunization with MBSA-γDPGA produced strong responses in some mice. Enhanced antibody responses were also observed in mice that were treated with the CD40 agonist antibody. This study demonstrated that use of CD40 agonist antibody was an effective and sufficient means to make antibodies to a polymeric antigen alone.

The ELISA procedure for detection of anti-γDPGA was exactly as described for detection of IgG antibodies to cryptococcal glucuronoxylomannan (Brandt, et al., CLIN. DIAG. LAB. IMMUNOL., 10:903-909 (2003)), with the exception that plates were coated with *Bacillus licheniformis* γDPGA. The ELISA can be further adapted for detection of antibody class and subclass by use of horseradish peroxidase-labeled class- and subclass-specific second antibodies (Southern Biotechnology, Birmingham, Ala.).

Example 3

Figure 2:
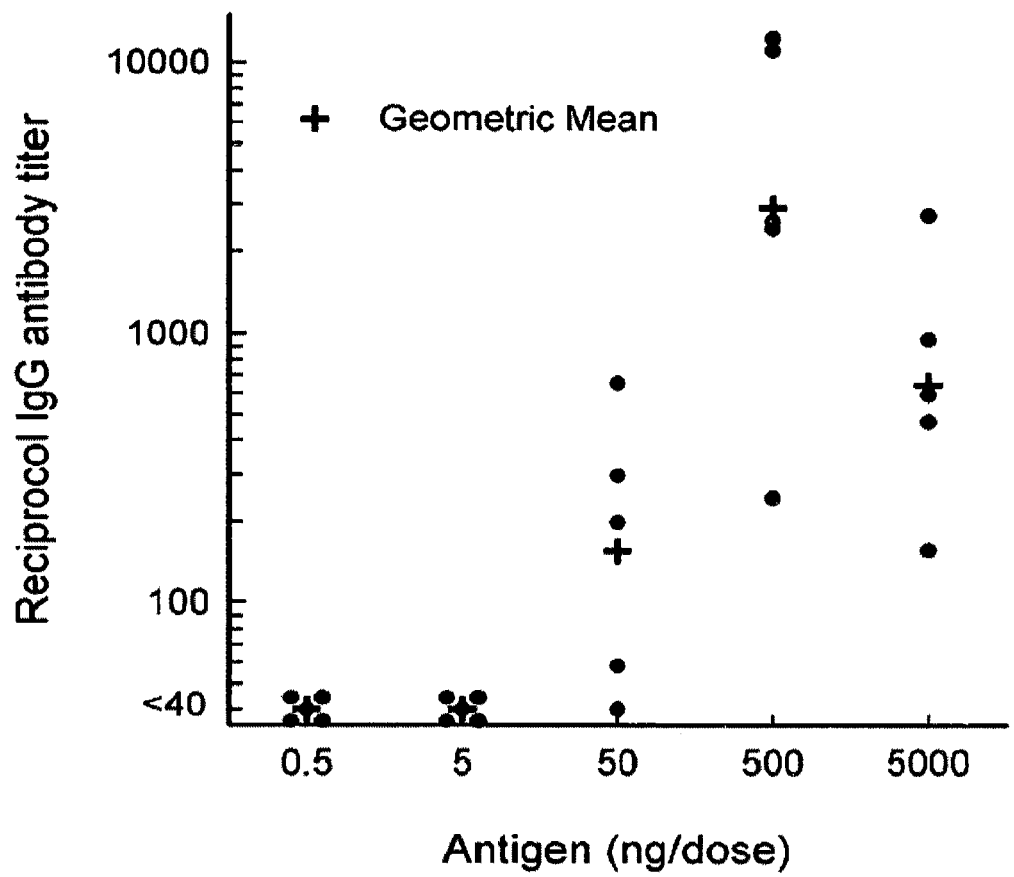
FIG. 2 illustrates the effect of antigen dose on the IgG antibody response to immunization with γDPGA in combination with CD40 agonist antibody (400 μg). Data shown are antibody titers from individual mice seven days after immunization.

Optimization of CD40 mAb Treatment for Enhancement of the Immune Response to γDPGA The antibody response produced by immunization with PGA in combination with CD40 agonist antibody demonstrated that the CD40 antibody was a potent adjuvant for generation of an immune response to γDPGA. In this example, a series of experiments was done to optimize the immunization protocol. In all instances, only anti-γDPGA IgG was measured. Other classes of antibodies can be similarly evaluated. The optimal antigen dose was first evaluated. Antibody levels were assessed 7 days after immunization. The results (FIG. 2) showed that immunization with 0.5 µg was optimal for mice. Reduced antibody levels were observed at higher and lower doses of γDPGA. There was little or no antibody response to immunization with 0.5 or 5 ng of γDPGA.

Figure 3:
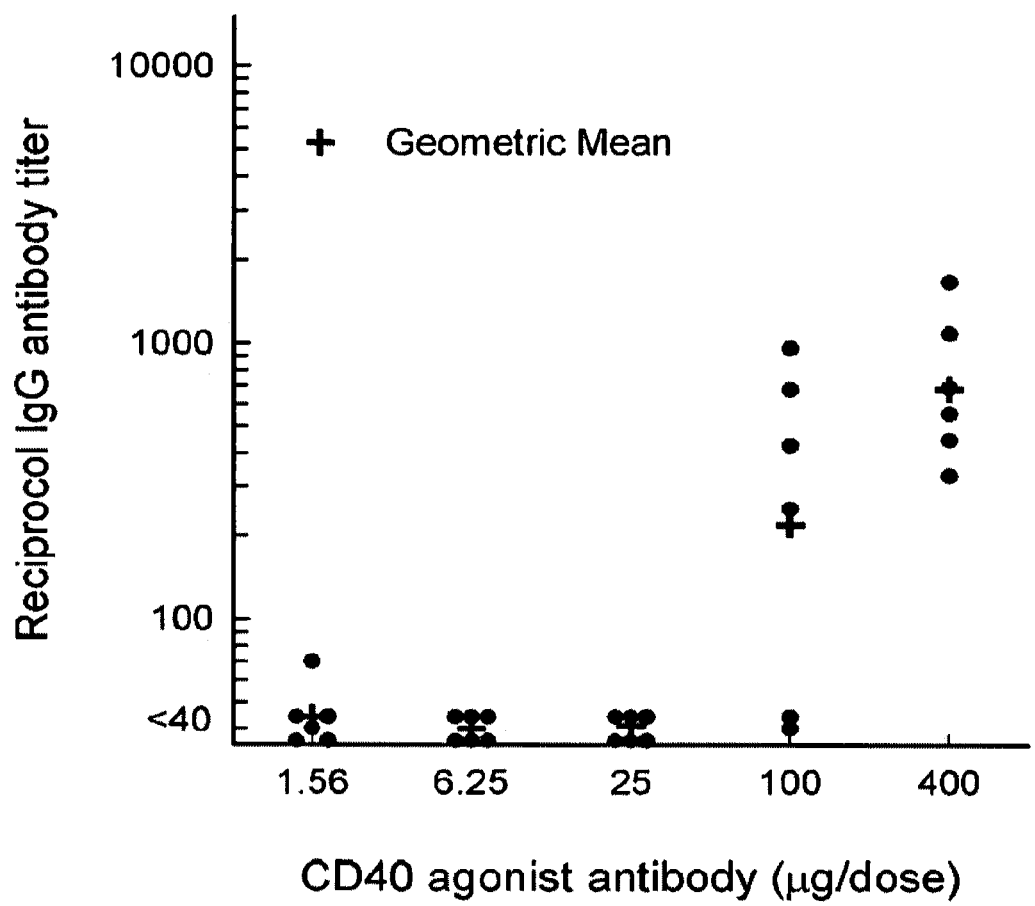
FIG. 3 demonstrates the effect of dose of CD40 agonist antibody on the IgG antibody response to immunization with γDPGA (0.5 μg). Data shown are antibody titers from individual mice seven days after immunization.

A second experiment evaluated the optimal dose of CD40 agonist antibody for immunization with 0.5 µg of γDPGA. The results (FIG. 3) showed that at least 400 µg of CD40 antibody was required for production of an optimized antibody response in mice.

The above experiments showed that optimal immunization occurs when mice are simultaneously immunized IP with a combination of 0.5 µg γDPGA and at least 400 µg agonist CD40 mAb.

Example 4

Immunization of Mice and Production of γDPGA mAbs

Figures 4A, 4B:
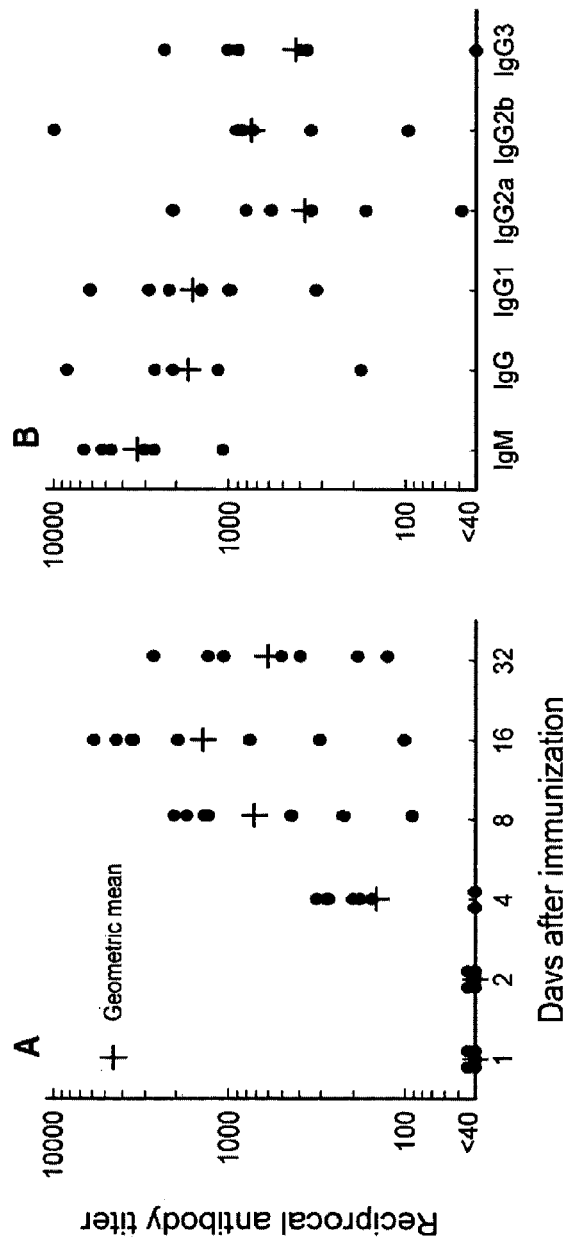
FIG. 4A illustrates the kinetics for production of anti-γDPGA IgG after immunization with *Bacillus licheniformis* γDPGA (0.5 μg) in combination with CD40 agonist antibody (400 μg). Data shown are γDPGA antibody titers for individual mice as well as the geometric mean titers.
FIG. 4B depicts levels of γDPGA antibodies of different isotypes 7 days after immunization with γDPGA in combination with CD40 agonist antibody. As in FIG. 4A, γDPGA antibody titers for individual mice as well as the geometric mean titers are shown.

BALB/c mice were immunized with *Bacillus licheniformis* γDPGA (0.5 µg) in combination with CD40 agonist antibody (400 µg). Most mice had detectable IgG anti-γDPGA four days after immunization and all mice were positive after 8 days (FIG. 4A). Examination of the IgG subclass of anti-γDPGA showed an IgG isotype-switched response seven days after immunization (FIG. 4B). These results further demonstrate that CD40 stimulation using an agonist antibody facilitates production of a serum antibody response to weak antigens.

Results from study of hybridomas generated from four mice showed a relatively low efficiency of production of hybridomas secreting anti-γDPGA from mice immunized with γDPGA+CD40 mAb alone (Table 2). The number of antibody-secreting hybridomas was increased more than 100-fold if mice were given a booster immunization 4 days before collection of spleens. Five cell lines that secrete anti-γDPGA were cloned by limiting dilution. Four of the five cell lines secreted anti-γDPGA IgG3. The CH gene for IgG3 is 5' to the CH gene for IgG1, IgG2b and IgG2a, allowing for generation of a full family of murine IgG subclasses.

Table 3 illustrates the results of an assessment of relative affinity among the five cell lines generated from the fusions described in Table 2. The affinities of mAbs F24G7 and F24F2 greatly exceed those of the monoclonal antibodies generated using the similar procedure against the capsular polysaccharide of *Cryptococcus neoformans* (mAb 3C2; aK=280). These results demonstrate the ability of CD40 mAb to produce an antibody response that is not only isotype switched, but also has an improved level of affinity maturation.

TABLE 2

Hybridoma Formation from Spleens of Mice Immunized with γDPGA in Combination with CD40 Agonist Antibody

| Fusion number[a] | Immunization protocol | IgM-secreting wells/total wells[b] | IgG-secreting wells/total wells[b] | Cell lines produced and cloned by limiting dilution |
|---|---|---|---|---|
| 21 | γDPGA + CD40 mAb (IP)[c] | Not tested | 1/192 | 21BL (IgG1) |
| 25 | γDPGA + CD40 mAb (IP)[d] | 0/192 | 0/192 | None |
| 24 | γDPGA + CD40 mAb (IP) + PGA IV boost[e] | 157/192 | 184/192 | F24G7 (IgG3), F24F2 (IgG3) |
| 26 | γDPGA + CD40 mAb (IP) + PGA IV boost[f] | 33/192 | 20/192 | F26G4 (IgG3), F26G3(IgG3) |

[a]Each fusion represents a mouse immunized by use of the indicated immunization protocol.
[b]After fusion, cells were distributed into 192 wells. The results indicate the number of wells containing colonies that secrete anti-γDPGA IgM or IgG.
[c]Spleens were harvested for hybridoma production 8 days after immunization with γDPGA + CD40 mAb.
[d]Spleens were harvested 29 days after immunization with γDPGA + CD40 mAb.
[e]Mice were given an intravenous booster immunization with 0.5 µg γDPGA 25 days after the initial immunization with PGA + CD40 mAb; spleens were harvested 4 days later.
[f]Mice were given an intravenous (IV) booster immunization with 1.0 µg γDPGA 17 days after the initial immunization with PGA + CD40 mAb; spleens were harvested 4 days later.

TABLE 3

Isotype and Affinity Constant (aK) of PGA mAbs

| mAb | Isotype | aK[a] |
|---|---|---|
| 21BL | IgG1 | 1.3 |
| F24G7 | IgG3 | 1300 |
| F24F2 | IgG3 | 1100 |
| F26G4 | IgG3 | 48 |
| F26G3 | IgG3 | 1400 |

[a]Relative (apparent) affinity constant (aK) was determined as described by Nieto, et al., MOL. IMMUNOL., 21: 537-543 (1984) and adapted for use with PGA.

One hybridoma that produced mAb F26G3 was selected for further study. This cell line adapted well to large scale antibody production in high concentrations in vitro. Reactivity of mAb F26G3 with soluble γDPGA and capsulated *Bacillus anthracis* was determined by double immunodiffusion in agar, DIC microscopy, and direct immunofluorescence microscopy (FIGS. 5A, 5B, and 5C, respectively). The precipitin line produced with γDPGA from *Bacillus licheniformis* was sharp and slightly concave toward the antigen well. γDPGA from *Bacillus anthracis* produced two precipitin lines, a broad diffuse band that was concave toward the antibody well and a weak line that was straight (FIG. 5A, arrow), suggesting the presence of two species of γDPGA of different molecular sizes. The high and low molecular weight forms were separated by resolubilizing the total γDPGA in sodium acetate buffer, and the high molecular weight γDPGA was precipitated by addition of one volume of ethanol. The low molecular weight γDPGA precipitated on addition of two more volumes of ethanol. Analysis of the high and low molecular weight precipitates by immunodiffusion showed that the two forms had been separated by this differential precipitation (FIG. 5A).

Examination of the binding of mAb F26G3 to capsulated *Bacillus anthracis* by DIC microscopy showed a quellung type capsular reaction (FIG. 5B). Similarly, direct immunofluorescence showed uniform binding of the antibody to the capsule of all cells (FIG. 5C).

The above experiments demonstrate that a single immunization with γDPGA in combination with CD40 agonist antibody leads to production of specific IgG antibodies as early as 4 days after immunization. Use of CD40 agonist antibodies to enhance T cell independent responses was first reported for *Streptococcus pneumoniae* capsular polysaccharide (Dullforce, et al., supra). The above results extend the enhancing effect of CD40 antibody to a capsular polypeptide and demonstrate that splenic lymphocytes from mice immunized in this manner produce antibody-secreting hybridomas when coupled with a booster immunization shortly before harvesting of spleen cells.

γDPGA for immunization was obtained from *Bacillus licheniformis* which was grown under conditions that stimulated production of PGA with the D isomer. A mAb that was generated from mice immunized in this manner was reactive with *Bacillus anthracis* γDPGA as shown by (i) precipitation in double immunodiffusion, (ii) a distinct quellung reaction and binding of fluorescently labeled mAb to whole bacterial cells, (iii) detection of γDPGA in sera of infected mice (see Example 5), and (iv) protection against pulmonary anthrax infection (see Example 6).

A difference between γDPGA isolated from *Bacillus licheniformis* and *Bacillus anthracis* was the appearance of the antigens in double immunodiffusion. *Bacillus licheniformis* γDPGA produced a single precipitin line with a shape that was consistent with having a high molecular weight. *Bacillus anthracis* γDPGA produced two precipitin lines; the shape of one line was consistent with the antigen having a low molecular weight and the other was consistent with a high molecular weight. The presence of low and high molecular weight γDPGA in culture filtrates of *Bacillus anthracis* was previously reported. These previous studies attributed the low molecular weight fraction to depolymerization of high molecular weight γDPGA by a depolymerase that is produced by *Bacillus anthracis*. Analysis of sera from infected mice by double immunodiffusion appears to show only the high molecular weight form of γDPGA (see Example 5). Absence of the low molecular weight form in serum could be due to a failure to depolymerize the high molecular weight form in vivo. Alternatively, the low molecular weight form could be rapidly cleared from serum.

Procedures for immunization of mice and production of γDPGA mAbs are provided below. Preliminary dose-response experiments established that improved serum levels of anti-γDPGA IgG were produced when BALB/c mice (Charles River Laboratories, Wilmington, Mass.) were immunized intraperitoneally with 0.5 µg of γDPGA from *Bacillus licheniformis* in combination with 400 µg of mAb FGK115, an agonist rat IgG2a anti-mouse CD40. Sera were collected at various times after immunization, and antibody levels were assessed by ELISA in which γDPGA from *Bacillus licheniformis* was coated onto microtiter plates.

For hybridoma formation, spleens were obtained from mice 8-29 days after immunization with γDPGA in combination with CD40 mAb. In some cases, mice were given an intravenous booster injection of 0.5 or 1.0 µg γDPGA in PBS 4 days before collection of spleens. Hybridomas were produced by fusion with the X63-Ag8.653 cell line using standard techniques. Cell lines were grown in tissue culture using a Tecnomouse hollow fiber culture system or an Integra CL 1000 culture flask (Integra Biosciences, Switzerland), and mAbs were isolated by affinity chromatography on protein A (Pierce, Rockford, Ill.). An irrelevant IgG3 mAb (mAb M600) reactive with the capsular polysaccharide of *Cryptococcus neoformans* serotypes A and D was used as an isotype control.

Binding of γDPGA mAbs to the *Bacillus anthracis* capsule was assessed by direct immunofluorescence and by the quellung reaction. The quellung reaction was determined by using DIC microscopy. Direct immunofluorescence used γDPGA mAb F26G3 that had been labeled with Alexa Fluor 488 (Molecular Probes). Microscopy was done with a Nikon Confocal Microscope C1 that was fitted to a Nikon Eclipse E800 microscope. Precipitin formation by soluble γDPGA and mAb F26G3 was assessed by double immunodiffusion in agar (Ouchterlony, ACTA PATHOL. MICROBIOL. SCAND., 25:186-191 (1948)).

Example 5

Production of Soluble γDPGA During Pulmonary Anthrax

Figures 6A, 6B:
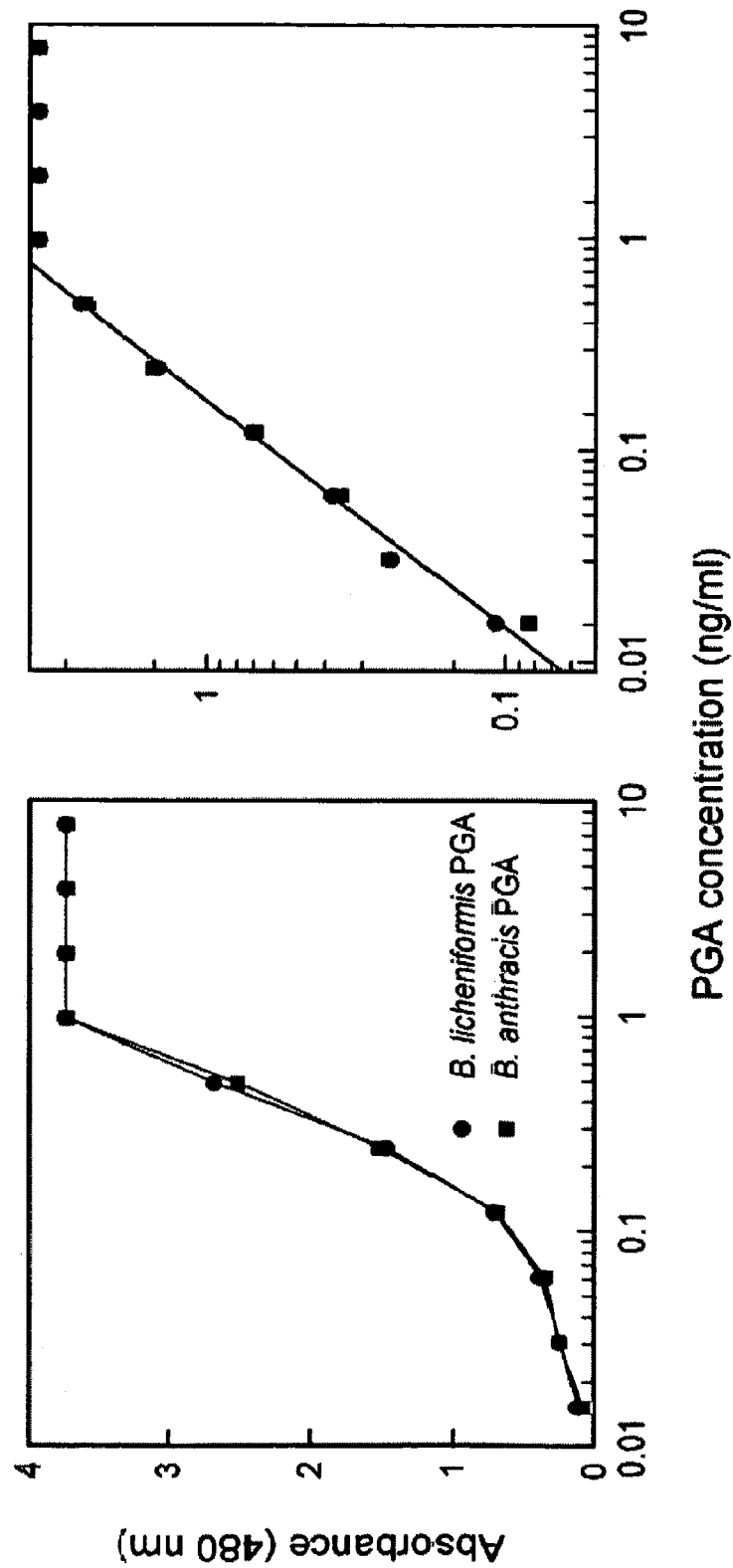
FIG. 6A illustrates an antigen capture ELISA for detection of *Bacillus licheniformis* γDPGA. Wells of a microtiter plate were coated with a dilution of anti-γDPGA mAb F26G3. The wells were blocked and incubated with various concentrations of purified γDPGA from *Bacillus licheniformis*. The wells were washed and incubated with horseradish peroxidase-labeled mAb F26G3. The wells were washed and incubated for 30 min with horseradish peroxidase substrate. Results are plotted as the $OD_{450}$ vs the concentration of γDPGA added to each well.
FIG. 6B shows the results from FIG. 6A plotted as log $OD_{450}$ vs the log of the concentration of γDPGA added to each well.

An antigen capture ELISA for detection of soluble γDPGA was constructed using mAb F26G3 in the capture phase and a horseradish peroxidase conjugate of mAb F26G3 as the indicator. Microtiter plates were coated with mAb F26G3, washed and incubated with various amounts of with γDPGA from *Bacillus licheniformis*. The plates were washed again, and incubated with mAb F26G3 that had been coupled to horseradish peroxidase (HRPO). A substrate for HRPO was added, and the $OD_{450}$ was measured after 30 min incubation. The results (FIG. 6) showed that the antigen capture assay could detect γDPGA at concentrations as low as 100-140 pg/ml. This limit of sensitivity is 10-100 times more sensitive than similarly constructed assays for the capsular polysaccharide of *Cryptococcus neoformans* and capsular polysaccharides of several pathogenic bacteria.

To assess production of γDPGA production during infection, mice were infected via the intratracheal route with 5 $LD_{50}$ of *Bacillus anthracis* spores. Sera were collected from three separate mice at each of 12, 24 and 48 h after infection. The sera were assayed for the presence of γDPGA using the antigen capture assay. The results are reported in Table 4 as the highest dilution of serum that produced an $OD_{450}$=0.5. These results indicate that γDPGA is shed in large amounts during pulmonary anthrax.

TABLE 4

Serum Titer for γDPGA after Infection of Mice with Anthrax[a]

| 12 h post infection | 24 h post infection | 48 h post infection |
|---|---|---|
| <1/20 | 1/46 | 1/590,000 |
| <1/20 | 1/670 | 1/1,900,000 |
| <1/20 | <1/20 | <1/20 |

[a]Nine mice were infected with 5 $LD_{50}$ at time zero. Three mice were sacrificed at each of the indicated times after infection. Results are expressed as the antigen titer. The antigen titer is defined as the highest dilution of serum that produces an $OD_{450}$ = 0.5 in an antigen titer capture ELISA using mAb F26G3 as both the capture and indicator antibody.

Note that there was variability between mice in the level of serum γDPGA. Such variability may reflect the inherent variability in instillation of the inoculum and variability in the course of disease in individual animals. The ability to accurately assess the state of disease is one of the advantages of the present invention.

Figure 7A:
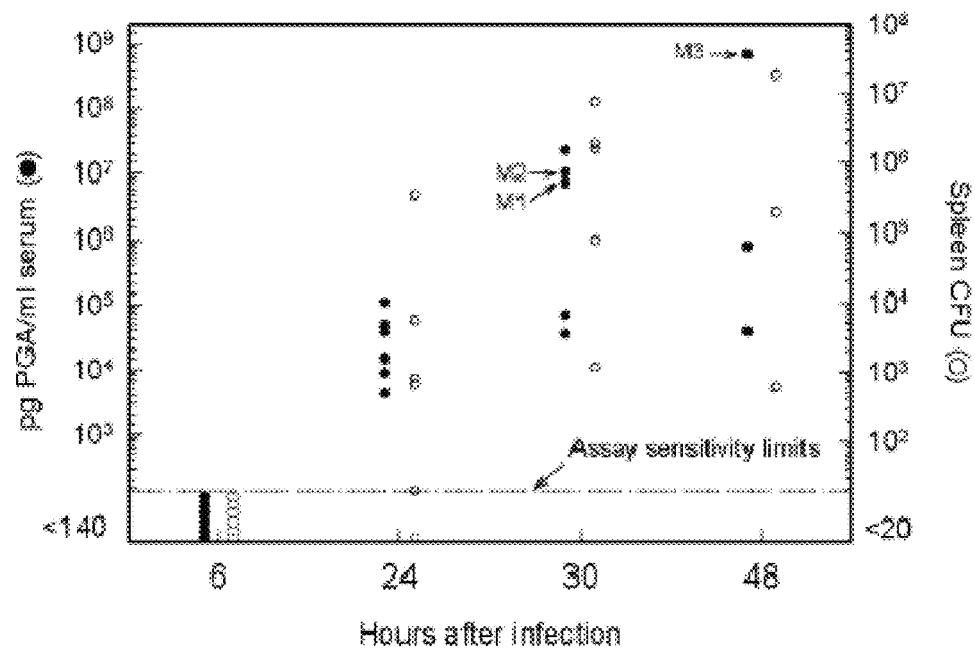
FIG. 7A demonstrates the detection of γDPGA antigenemia and *Bacillus anthracis* bacteremia as shown by splenic colony forming units (CFU) following intratracheal challenge with 5 $LD_{50}$ (the dose lethal to 50% of the population tested) *Bacillus anthracis* spores. Animals were sacrificed at the indicated time after infection. Serum antigen levels (•) are reported as pg γDPGA per ml using purified γDPGA from *Bacillus licheniformis* as a standard (left axis). Results from quantitative organ culture (o) are shown as total CFU per spleen (right axis).
Figure 7B:
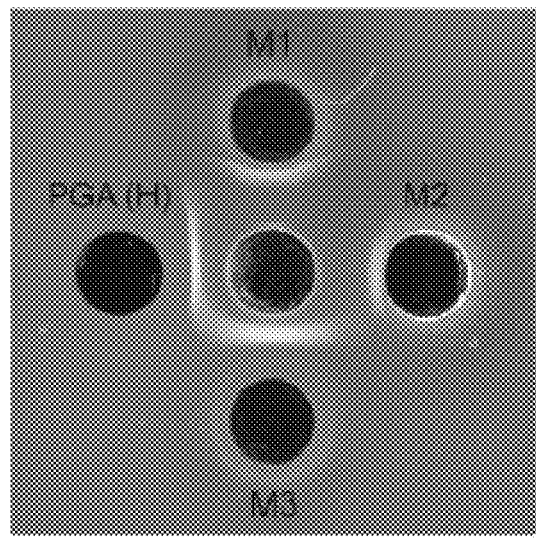
FIG. 7B reveals double immunodiffusion showing reactivity of mAb F26G3 with undiluted serum from infected mice (M1, M2, and M3 in FIG. 7A, which have concentrations of 7.3, 11 and 670 μg γDPGA per ml, respectively) or the high molecular weight fraction of *Bacillus anthracis* γDPGA ("PGA (H)").

To assess the correlation between the appearance of antigenemia and the time of dissemination following pulmonary infection, mice were infected via the intratracheal route with 5 $LD_{50}$ of *Bacillus anthracis* spores (Ames strain). Five or six mice were sacrificed at 6, 24, 30 or 48 h after challenge. Spleens were harvested for quantitative organ culture, and serum was prepared for analysis of γDPGA content (FIGS. 7A and 7B). At 24 h after challenge, antigenemia was detected in all animals; culture of spleen was positive for five of six mice. An additional result shown in FIG. 7A is the high level of antigenemia that occurs in disseminated anthrax. One mouse (M3 in FIG. 7A) showed a TDPGA titer of 1/5,000,000. Such a titer corresponds to approximately 600 μg γDPGA per ml.

Antigenemia produced during pulmonary anthrax is also demonstrated in FIG. 7B where sera from three infected mice were examined by double immunodiffusion. Prominent precipitin lines were produced. The position of the lines reflected the γDPGA concentration in each of the sera. The shape of the precipitin lines is similar to the high molecular weight γDPGA isolated from *Bacillus anthracis* grown in vitro (FIG. 5A).

Figure 8:
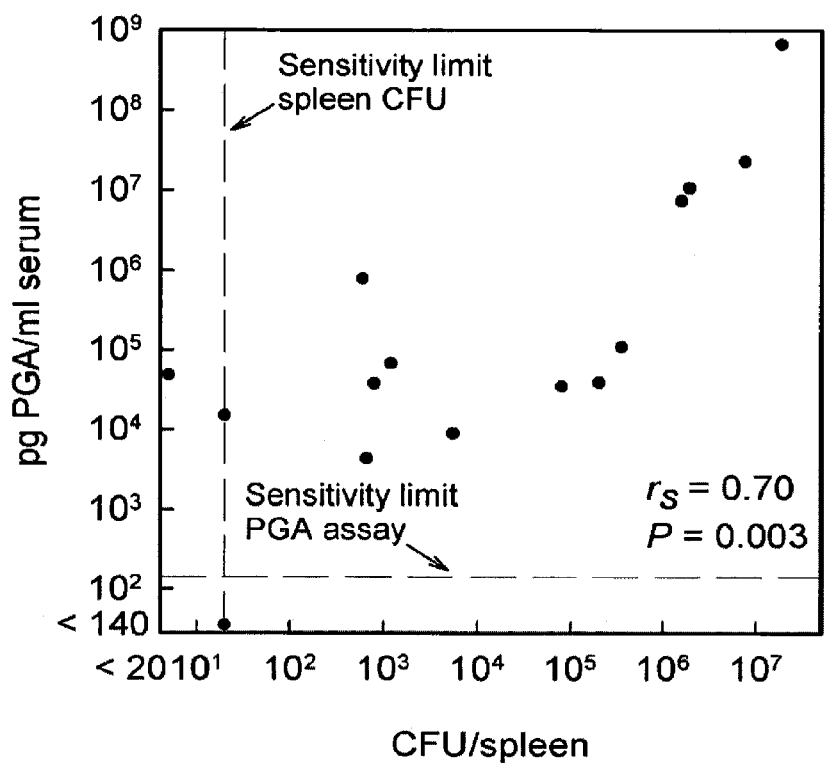
FIG. 8 illustrates the correlation between levels of antigenemia (pg γDPGA per ml serum) and bacteremia (spleen CFU) for individual mice. Results are presented from all mice shown in FIG. 7A regardless of the time after infection at which the samples were taken. Correlation was determined by Spearman rank correlation coefficient.

Results from all mice in FIG. 7A that had either a positive test for bacteremia (positive spleen culture) or antigenemia ($OD_{450}$≧0.5) are shown in FIG. 8. Antigen concentration in serum is plotted as a function of CFU in spleen for each mouse. The results showed a correlation ($r_s$=0.70; P=0.003) between results from the two assays. Despite the correlation for the group of mice, there were several instances where bacteremia levels exceeded antigenemia levels in individual mice or vice versa. In particular, there were two mice that showed considerable antigenemia, but the spleen cultures were at or below the level of detection.

Little is known about production of soluble γDPGA during anthrax. This example used γDPGA mAb F26G3 for construction of an antigen capture immunoassay for detection of soluble antigen. The assay had a detection limit of approximately 100 pg per ml. Use of the immunoassay for analysis of sera from infected mice showed that antigen appears at a time after infection that coincides with the appearance of bacteremia as shown by splenic CFU. As the infection progressed, assay for antigenemia closely paralleled results of splenic culture, suggesting that immunoassay for γDPGA is a useful surrogate for blood culture in assessment of *Bacillus anthracis* infection. In the latter stages of infection, high levels of serum γDPGA were observed, reaching concentrations of greater than 500 μg/ml.

Evaluation of factors influencing patient outcome in the 2001 anthrax attack showed that early recognition of infection and prompt administration of antibiotics were closely associated with patient survival. A report of two patients who died of bioterrorism-related inhalation anthrax emphasized the need for specific diagnostic tools that can be used in the clinical setting where infection is likely to be encountered. Immunoassays for bacterial capsular antigens in body fluids are well known in the art. Such assays, are generally inexpensive, sensitive, rapid, and easy to perform by untrained personnel. The finding of readily measurable levels of γDPGA early in infection at the time of emergence of bacteremia suggests that γDPGA detection is a means for early diagnosis of anthrax.

One procedure for construction of the antigen capture immunoassay is provided below. Microtiter plates were coated overnight with γDPGA mAb F26G3 in PBS (0.75 μg/ml), washed with PBS-Tween (PBS containing 0.05% Tween 20), and blocked by incubation for an additional 90 min with PBS-Tween. Serial dilutions of γDPGA or sera from infected mice were prepared in PBS-Tween and incubated for 90 min at room temperature with the antibody-coated wells. The wells were washed with PBS-Tween, incubated for 90 min with horseradish peroxidase-labeled (Pierce, Rockford, Ill.) γDPGA mAb F26G3 (0.2 μg/ml), washed and incubated with tetramethyl benzidine substrate (Kirkegaard & Perry Laboratories, Inc., Gaithersburg, Md.). The data are reported as pg of γDPGA per ml using *Bacillus licheniformis* γDPGA as a standard. An $OD_{450}$ of 0.5 was used as the limit of assay sensitivity.

For the construction of murine model of pulmonary anthrax, a spore inoculum was first prepared. A starter culture was prepared by inoculating PA broth (Dixon, et al., CELL MICROBIOL., 2:453-463 (2000)) with a colony of *Bacillus anthracis* (Ames strain) from a blood agar plate and incubated overnight at 37° C. on a shaker at 350 rpm. Large scale culture was prepared by inoculating fresh PA broth with a portion of the starter culture (1:40 ratio), and incubated for 24 h at 37° C. on a shaker at 350 rpm. Sterile distilled water was added, and the incubation was continued for an additional 40-80 h. After 40 h incubation, the cultures were examined periodically by phase contrast microscopy to confirm complete sporulation and the absence of vegetative cells. The spore preparation was then heated at 68° C. for 40 min to eliminate trace contamination with vegetative forms. Aliquots of the spore suspension were frozen at −80° C., and the titer of the spore stock was determined by quantitative culture on blood agar plates.

BALB/c mice (Harlan, Indianapolis, Ind.) were used for pulmonary anthrax studies. To challenge the mice, frozen spore stocks were thawed and diluted in sterile PBS to the appropriate concentration for intratracheal delivery. Mice were anesthetized with avertin and a 50 μl inoculum containing 5 $LD_{50}$ (approximately 5000 spores) was instilled into the lungs via the intratracheal route. Mice were observed twice daily for death.

Quantitative culture of spleen was used as an indicator for bacteremia. Mice were euthanized, spleens were harvested and homogenized in 1 ml of PBS, and quantitative plate cultures were prepared from 50 μl of splenic homogenate or a serial dilution of homogenate. The sensitivity limit for determination of splenic CFU was approximately 20 CFU/spleen.

Example 6

Immunoprotection by γDPGA mAb Against Inhalation Anthrax

Figures 9A, 9B:
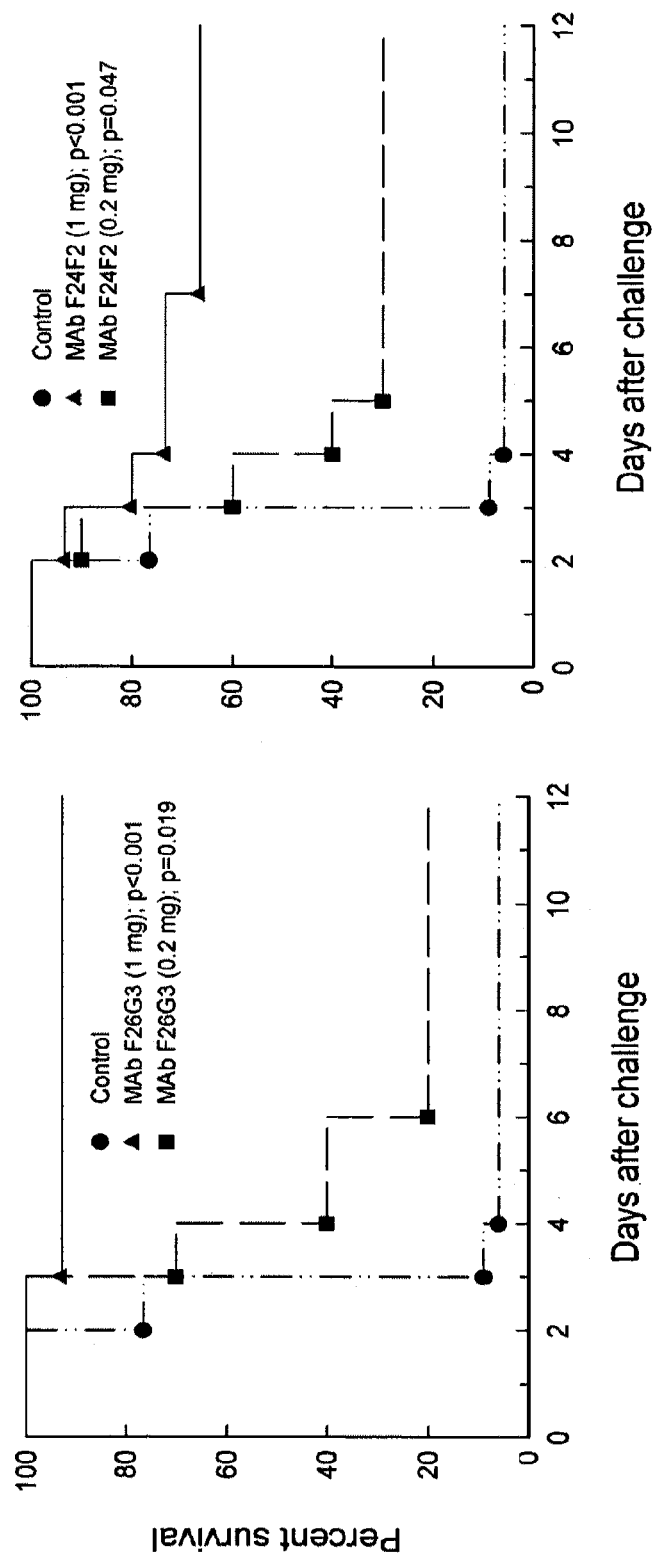
FIG. 9A demonstrates the effect of passive immunization with mAb F26G3 on survival of mice following intratracheal challenge with approximately 5 $LD_{50}$ of *Bacillus anthracis* spores. Results shown are the combined data from two independent experiments. Mice were treated 18 h before challenge by intraperitoneal (IP) injection of phosphate buffered saline (PBS) (5 mice in Exp #1 and 10 mice in Exp #2), 1 mg irrelevant isotype control (IgG3) mAb M600 (10 mice in Exp #2), 0.2 mg γDPGA mAb F26G3 (10 mice in Exp #2; P<0.05 vs control mice), or 1 mg γDPGA mAb F2603 (4 mice in Exp #1 and 10 mice in Exp #2; P<0.0001 vs control mice).
FIG. 9B demonstrates the effect of passive immunization with mAb F24F2 on survival of mice following intratracheal challenge with approximately 5 $LD_{50}$ of *Bacillus anthracis* spores. Mice were treated 18 h before challenge by intraperitoneal (IP) injection of phosphate buffered saline (PBS), 1 mg irrelevant isotype control (IgG3) mAb M600, 0.2 mg γDPGA mAb F24F2, or 1 mg γDPGA mAb F24F2.

Mice were treated by intraperitoneal injection of 1 mg or 200 μg of the IgG3 γDPGA mAb F26G3. Controls were PBS or an irrelevant IgG3 mAb that is reactive with the capsular polysaccharide of *C. neoformans* (mAb M600). Mice were challenged 18 h after mAb treatment by intratracheal instillation of approximately 5 $LD_{50}$ of spores from the Ames strain of *Bacillus anthracis*. The results showed that 90% of control mice died rapidly, within 3 or 4 days after challenge (FIG. 9A). Greater than 90% of mice given 1 mg of the γDPGA mAb survived (P<0.0001 vs control mice). Partial protection was observed in mice passively immunized with 200 μg of the γDPGA mAb where a significant extension of survival time was observed relative to control mice (P<0.04).

In another experiment, mice were passively immunized by intraperitoneal injection of 1 mg or 200 μg of mAb F24F2. The mice were challenged 12 h later via the intratracheal route with 5 $LD_{50}$ of *Bacillus anthracis* spores. The results (FIG. 9B) showed a significant level of protection (P<0.001) in mice given 1 mg of mAb F24F2. A lesser level of protection was afforded to mice given 200 μg of mAb.

The survival curves in FIGS. 9A and 9B were analyzed by using Kaplan-Meier estimators. The survival curves were compared using the log-rank test; and pairwise multiple comparisons were done with P values adjusted for these multiple comparisons by the Bonferroni method. Correlation coefficients (FIG. 8) were determined by the Spearman rank correlation coefficient.

The high level of protection afforded by passive immunization with a γDPGA mAb identifies γDPGA as a target for active or passive immunization. The current anthrax vaccine adsorbed (AVA) is aimed at anthrax toxins. The extent to which a toxin-based immunity alone can protect against the potential large inoculum that might occur in a bioterrorism attack is not known. One approach to an improved vaccine formulation is a conjugate vaccine that targets both the antiphagocytic capsule and the toxin. The results of this example provide support for targeting γDPGA in a vaccine formulation and suggest efficacy of passive immunization in individuals who have not been immunized.

Example 7

Anti-γDPGA Antibodies in Adult Humans

Sera of 33 normal adults were examined by using the ELISA assay described in Example 2. PGA is produced by several *Bacillus* species that are likely to be encountered in the environment. Such exposure to either saprophytic *Bacillus* species or to *Bacillus anthracis* itself would lead to production of PGA antibodies. This is a common phenomenon in which exposure to naturally-occurring antigens leads to eventual production of high levels of antibodies to many capsular polysaccharides.

Figure 10:
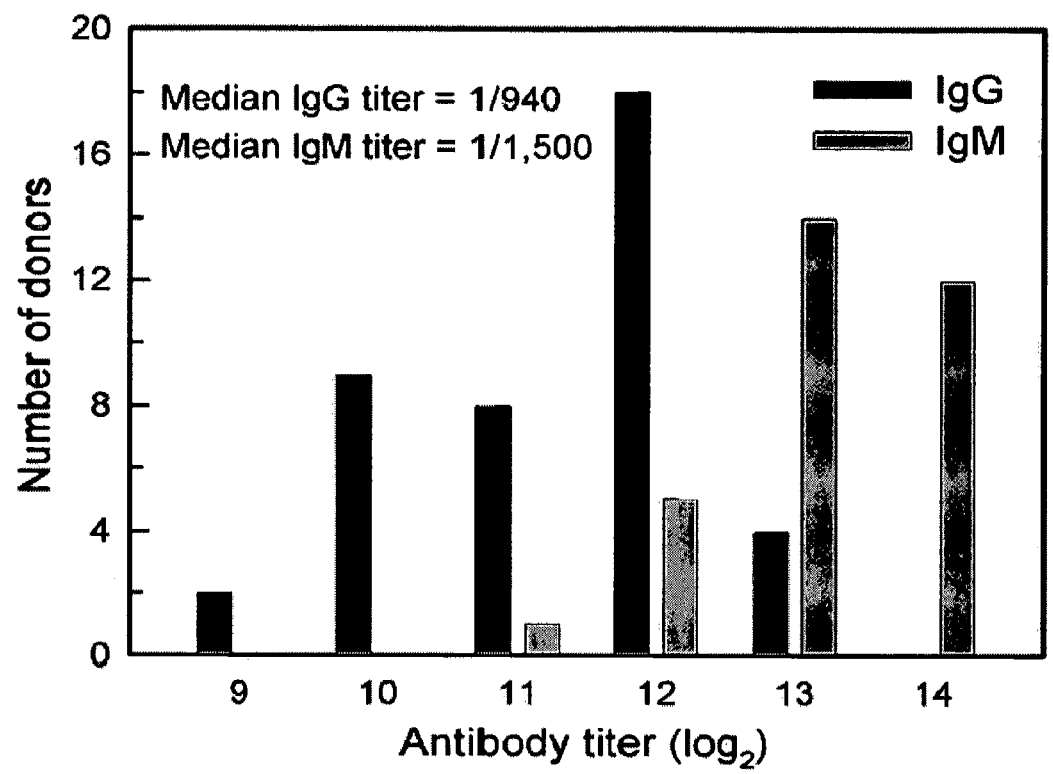
FIG. 10 is a histogram showing numbers of adult humans with various levels of anti-γDPGA IgG and IgM antibodies. Results are shown for 33 normal adult volunteers.

The results showed that normal adults produce anti-γDPGA IgG and IgM (FIG. 10). The titers are normally distributed; some individuals have quite high levels of antibody. These results have at least three implications. First, the results indicate that γDPGA is a suitable antigen for detection of antibody in an ELISA format. Second, these results indicate that normal adults can generate γDPGA antibodies. Third, the presence of relatively high levels of antibody in some sera suggests that γDPGA antibodies are not harmful. This is an important consideration for either active or passive immunization that targets γDPGA.

What is claimed is:

1. A method comprising administering poly γ-D-glutamic acid and a CD40 agonist to a vertebrate according to a regime such that an immune response is elicited in the vertebrate against *Bacillus anthracis*.

2. The method according to claim 1, wherein the CD40 agonist is an agonistic anti-CD40 antibody.

3. The method according to claim 1, wherein an administration of the CD40 agonist is simultaneous with, or separated by no more than 24 hours from, an administration of said poly γ-D-glutamic acid.

4. The method according to claim 1, comprising at least one booster administration of said poly γ-D-glutamic acid after an initial administration of said poly γ-D-glutamic acid and the CD40 agonist.

5. The method according to claim 1, wherein said vertebrate is a human.

6. The method according to claim 1, wherein the poly γ-D-glutamic acid is isolated from *Bacillus anthracis*.

7. The method according to claim 1, wherein the poly γ-D-glutamic acid is isolated from *Bacillus lichenformis*.

8. The method according to claim 1, further comprising establishing an anti-γDPGA antibody producing hybridoma from the vertebrate.

9. The method according to claim 8, further comprising isolating anti-γDPGA antibodies from the hybridoma.

* * * * *